US006264991B1

(12) United States Patent
Barrow et al.

(10) Patent No.: US 6,264,991 B1
(45) Date of Patent: Jul. 24, 2001

(54) COMPOSITIONS AND METHODS FOR TREATING INTRACELLULAR INFECTIONS

(75) Inventors: William W. Barrow; Esther L. Barrow, both of Hoover; Debra C. Quenelle, Wilsonville; Gary A. Winchester, Birmingham; Jay K. Staas, Alabaster, all of AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/135,708

(22) Filed: Aug. 18, 1998

(51) Int. Cl.$^7$ .................................. A61K 9/50; A61F 2/02
(52) U.S. Cl. ........................... 424/501; 424/426; 424/502
(58) Field of Search ..................................... 424/426, 409, 424/501, 502; 514/772.3

(56) References Cited

U.S. PATENT DOCUMENTS

| | | |
|---|---|---|
| 5,384,133 | 1/1995 | Boyes et al. . |
| 5,407,609 | 4/1995 | Tice et al. . |

FOREIGN PATENT DOCUMENTS

| | | |
|---|---|---|
| 0330180 A1 | 8/1989 | (EP) . |
| 0333523B1 | 9/1989 | (EP) . |
| 0752245 A1 | 1/1997 | (EP) . |
| WO 86/02002 | 4/1986 | (WO) . |
| WO 91/09616 | 7/1991 | (WO) . |

OTHER PUBLICATIONS

Barrow et al., Antimicrob. Agents Chemother., 42(10), pp. 2682–2689, 1998 (Abstract).

Peter Stjarnkvist et al., Biodegradable microspheres. VIII. Killing of Leishmania donovani in cultured macrophages by microparticle–bound primaquine, International Journal of Pharmaceutics, vol. 40, pp. 215–222, (1987).

E. L. Wright et al., Use of Mono Mac 6 Human Monocytic Cell Line and J774 Murine Macrophage Cell Line in Parallel Antimycobacterial Drug Studies, Antimicrobial Agents and Chemotherapy, vol. 40, No. 9, pp. 2206–2208, (Sep. 1996).

T. R. Tice et al., Development of Microencapsulated Antibodies for Topical Administration, 13$^{th}$ International Symposium on Controlled Release of Bioactive Materials, (Aug. 1986).

Optimum Treatment of Intracellular Infections is Based on Clinical Data, Drugs & Therapy Perspectives, 10(11):8–11, (1997).

Elliot Jacob et al., Evaluation of Biodegradable Ampicillin Anhydra Microcapsules for Local Treatment of Experiment *Staphylococcal Osteomyelitis*, Clinical Orthopaedics and Related Research, No. 267, pp. 237–244, (Jun., 1991).

J. M. Quigg et al., Synthesis Properties and Intratumoral Evaluation of Drug Loaded Protein Microspheres, Proceed Intern. Symp. Control. Rel. Bioact. Mater., vol. 19, pp. 156–157, (1992).

Hideya Kimura et al., In vitro phagocytosis of polylactide microspheres by retinal pigment epithelial cells and intracellular drug release, Current Eye Research vol. 13, pp. 353–360, (1993).

A. Bender et al., Inhibition of HIV in vitro by antiviral drug–targeting using nanoparticles, Res. Virol. vol. 145, pp. 215–220, (1994).

(List continued on next page.)

*Primary Examiner*—Carlos A. Azpuru
(74) *Attorney, Agent, or Firm*—Needle & Rosenberg, P.C.

(57) ABSTRACT

A method of treating or preventing an intracellular infection in an animal comprising administering a first effective amount of a suitable drug contained in first biocompatible microspheres that have a diameter of less than or equal to about 10 microns, wherein the first microspheres release the suitable drug upon administration at a first effective rate. A second set of microspheres greater than 10 microns in diameter may also be administered to provide continuing systemic release of the drug.

48 Claims, 10 Drawing Sheets

OTHER PUBLICATIONS

Jayant Karajgi et al., Passive Vectoring of Colloidal Carrier System for Sodium Stibogluconate: Preparation, Characterization and Performance Evaluation, Journal of Drug Targeting, vol. 1, pp. 197–206, (1993).

J. Kreuter, Liposomes and Nanoparticles As Vehicles for Antibiotics, Journal for the Clinical Study and Treatment of Infections, vol. 19, S 224–228, (1991).

S. Pande et al., Localized rifampicin albumin microspheres, J. Microencapsulation, vol. 8, No. 1, pp. 87–93, (1991).

John R. Graybill, M.D., Lipid Formulations for Amphotericin B: Does the Emperor Need New Clothes?, Annals of Internal Medicine, vol. 124, No. 7, pp. 921–923, (Apr. 1, 1996).

Irma A.J.M. Bakker–Woudenberg, Delivery of antimicrobials to infected tissue mcrophages, Advanced Drug Delivery Reviews, vol. 17, pp. 5–20, (1995).

M. C. Venier–Julienne, In Vitro Study of the Anti–Leishmanial Activity of Biodegradable Nanoparticles, Journal of Drug Targeting, vol. 3, pp. 23–29, (1995).

010.0μ

010.0μ

100.0μ

001.0μ

010.0μ

COMPOSITIONS AND METHODS FOR TREATING INTRACELLULAR INFECTIONS

ACKNOWLEDGMENTS

This invention was made with government support under Grant AI38185 awarded by the National Institutes of Health. The government has certain rights in the invention.

BACKGROUND OF THE INVENTION

1. Field of the Invention

This invention relates generally to methods and compositions for treating intracellular infections and to microsphere preparations used for such treatment.

2. Background Art

Diseases associated with intracellular infections often do not respond adequately to conventional drug treatment regimens, causing many patients to suffer relapses after being treated for such diseases. A wide array of drugs are used to treat diseases associated with intracellular infections. In addition, much research is devoted to identifying new drugs to treat such diseases. However, conventional drugs and drug treatments are often limited by toxicity which, for many drugs, is very close to the minimum inhibitory concentration of the drug, thus giving a very narrow window of drug efficacy. Treatment regimens also typically involve multiple doses, increasing the risk of treatment failure caused by patient noncompliance.

The present invention provides a unique regimen of compositions and methods for treating all intracellular infections, using any drug suited for the particular disease. The regimen of this invention targets drugs to infected cells, and is more successful treating intracellular infections than conventional regimens. The regimen of this invention reduces intracellular counts better than equivalent doses administered in conventional treatment regimens. The regimen of compositions and methods also requires fewer administrations, thus minimizing the risk of patient noncompliance.

SUMMARY OF THE INVENTION

In accordance with the purpose(s) of this invention, as embodied and broadly described herein, the invention, in one aspect, relates to a method of treating or preventing an intracellular infection in an animal in need of such treatment or prevention comprising administering to the animal a first effective amount of a first suitable drug contained in first biocompatible microspheres that have a diameter of from about 1 to about 10 microns, wherein the first microspheres release the first suitable drug upon administration at a first effective rate.

In another aspect the invention relates to a method of treating or preventing an intracellular infection in an animal in need of such treatment or prevention comprising administering to the animal a first effective amount of a first suitable drug contained in first biocompatible microspheres that have a diameter of less than or equal to 10 microns, wherein the first microspheres release the first suitable drug upon administration at a first effective rate.

In another embodiment the invention provides a composition for treating an intracellular infection in an animal comprising an effective amount of a suitable drug contained within biocompatible microspheres, wherein the microspheres have a diameter from about 1 to about 10 microns, and release the suitable drug upon administration at an effective rate.

In still another aspect the invention provides a kit for treating an intracellular infection in a patient comprising (a) an effective amount of a suitable drug contained within first biocompatible microspheres that release the suitable drug upon administration at a first effective rate, and (b) an effective amount of a suitable drug contained within second biocompatible microspheres that release the suitable drug upon administration at a second effective rate, wherein the first microspheres have a diameter from about 1 to about 10 microns, and the second microspheres have a diameter greater than about 10 microns, and wherein the drug may be the same or different for the first and second microspheres.

In another embodiment the invention provides a method for reducing the toxicity of a suitable drug used to treat intracellular infections comprising encapsulating a first effective amount of the suitable drug in first biocompatible microspheres that have a diameter of from about 1 to about 10 microns, and administering the microspheres to an animal, wherein the first microspheres release the suitable drug upon administration at a first effective rate.

In a still further embodiment the invention provides a method of making a drug formulation having reduced toxicity comprising encapsulating a first effective amount of the suitable drug in first biocompatible microspheres that have a diameter of from about 1 to about 10 microns.

Additional aspects and advantages of the invention will be set forth in part in the description which follows and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 7C depicts a cross section of a single microsphere. Bars represent 100, 1.0, and 10.0 micrometers respectively.

DEFINITIONS AND USE OF TERMS

Figure 1:
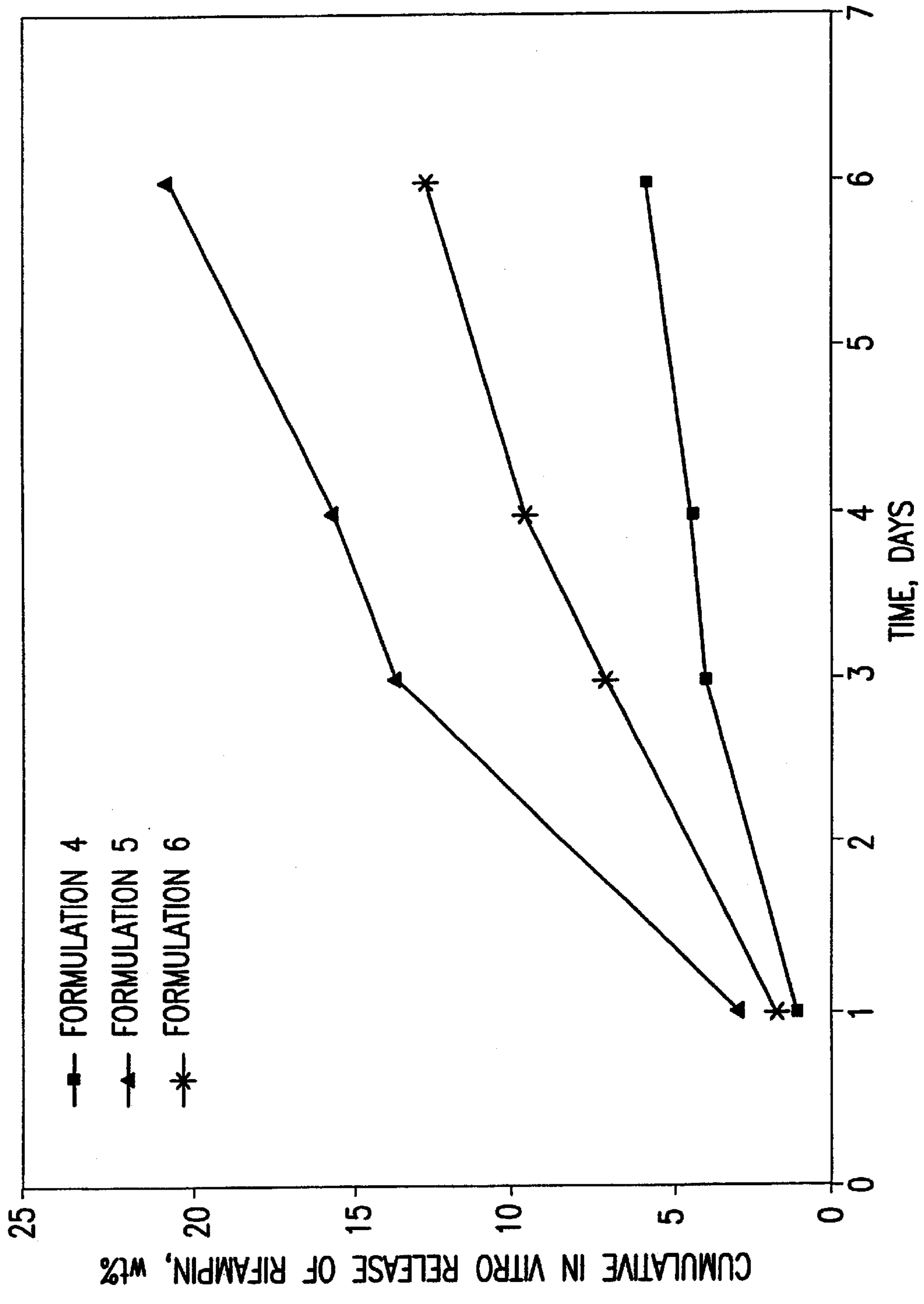
FIG. 1 shows the in vitro release characteristics of rifampicin-loaded microsphere formulations 4, 5, and 6 from Example 1 over a six-day period in receiving fluid.

In this specification and in the claims which follow, reference is made to a number of terms which shall be defined to have the following meanings:

As used in the specification and the appended claims, the singular forms "a," "an" and "the" include plural referents unless the context clearly dictates otherwise. Thus, for example, reference to "a microsphere" includes mixtures of microspheres, reference to "a dosage form" includes mixtures of two or more dosage forms, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

"Optional" or "optionally" means that the subsequently described event or circumstance may or may not occur, and that the description includes instances where said event or circumstance occurs and instances where it does not. For example, the phrase "optionally modified poly(lactide-co-glycolide)" means that the polymer may be modified with other acidic residues and that the description includes both modified and unmodified poly(lactide-co-glycolide) polymer.

By the term "effective amount" of a compound (e.g., drug) or property as provided herein is meant such amount as is capable of performing the function of the compound or property for which an effective amount is expressed. In addition, "effective rate" as used herein means the rate of administration of the compound (e.g., drug) or composition of this invention which results in achievement of the desired effect (e.g., treatment or prevention of infection). The exact amount required and the rate of administration will vary from process to process, depending on recognized variables such as the compounds employed and the processing conditions observed, as set forth herein. Thus, it is not possible to specify an exact effective amount or effective rate. However, an appropriate effective amount and effective rate may be determined by one of ordinary skill in the art using only routine experimentation.

By "pharmaceutically acceptable" is meant a material that is not biologically or otherwise undesirable, i.e., the material may be administered to an individual along with the selected compound or drug of this invention without causing any unacceptable biological effects or interacting in an unacceptable deleterious manner with any of the other components of the pharmaceutical composition in which it is contained.

The term biocompatible is defined as a material that is not toxic to the body, is not carcinogenic, and should not induce inflammation in body tissues. It is preferred that the microspheres of this invention be biodegradable in the sense that they are biocompatible and that they should degrade by bodily processes to products that are readily disposable by the body and should not accumulate in the body.

"Tuberculosis," or "TB," refers to any infection or disease in which the etiological agent is a member of the tuberculosis complex, such as *Mycobacterium tuberculosis, M bovis,* and *M africanum.* "Tuberculosis" preferably refers to any infection or disease in which the etiological agent is *Mycobacterium tuberculosis.*

The term "microsphere" is not meant to be limiting and includes any compound-carrying (e.g., drug-carrying) particulate or granular material within the particular size range recited. Microspheres are usually powders consisting of particles 2 millimeters or less in diameter, more usually 500 microns or less in diameter. The term "microsphere" also includes particles and material less than 1 micron, although these particles are often referred to as nanospheres. The term "microsphere" as used in the specification includes conventional microspheres (in which the drug is contained throughout an excipient matrix), microcapsules (in which the excipient forms a skin or shell that surrounds and contains the drug), and microparticles, which is used as a generic term for any particles in the recited size range, whether spherical or not, as those terms are typically used in the art.

DETAILED DESCRIPTION OF THE INVENTION

In one aspect the invention provides a method of treating or preventing an intracellular infection in an animal in need of such treatment or prevention comprising administering a first effective amount of a first suitable drug contained in first biocompatible microspheres that have a diameter of from about 1 to about 10 microns (sometimes "small microspheres"), wherein the first microspheres release the suitable drug upon administration at a first effective rate. The method has particular application to treating intracellular infections that reside in the macrophage and other phagocytic cells such as Kupffer's cells, monocytes and neutrophils. In one particular embodiment the first biocompatible microspheres have a diameter of from 1 to 5 microns. In another particular embodiment the first biocompatible microspheres have a diameter of from 5 to 10 microns. In still another embodiment the first biocompatible microspheres have a diameter less than or equal to 10 micrometers. In other embodiments the microspheres have a diameter within the range of from 1 to 10 microns, but more particularly greater than 2, 3, 4, 5, or 6 microns, and/or less than 9, 8, 7, 6, 5, or 4 microns. All microspheres within the range of 1 to 10 microns are included within the term "small microspheres" as that term is used herein.

The compositions and methods of the present invention can be used to treat infection by any facultative or obligate intracellular prokaryotic pathogen (e.g., pathogenic bacteria, rickettsia and chlamydia). For example, the compositions and methods of this invention can be used to treat intracellular infections caused by organisms which can include, but are not limited to, rickettsia (e.g., members of the spotted fever group [tick typhus], *Rickettsia typhi*), *Coxiella burnetti* (e.g., causative agents of Q fever), *Chlamydia trachomatis, Chlamydia psittaci, Chlamydia pneumoniae, Ehrlichia chaffeensis,* Legionella species (e.g., causative agents of legionellosis), Brucella species (e.g., causative agents of brucellosis, *Brucella melitensis*), Salmonella species (e.g., *Salmonella typhi, Salmonella enteritis*), Yersinia species (e.g., causative agents of Yersiniosis enteritis), Mycoplasma species (e.g., *Mycoplasma hominis, Ureaplasma urealyticum, Mycoplasma pneumoniae*), Bacillus species (e.g., causative agents of bacillary angiomatosis), Anaplasma species, Borrelia species (e.g., *Borrelia burgdorferi*), *Treponema pallidum* and Baronella species (e.g., causative agents of Baronella endocarditis, *Baronella bacilliformis*).

In a preferred embodiment, the compositions and methods of this invention are used to treat facultative mycobacterial infections especially including, for example, tuberculosis (particularly infection by *Mycobacterium tuberculosis*), and infection by *Mycobacterium avium.*

The methods and compositions of this invention can be used to treat any animal in which intracellular infections can occur, including companion animals such as canine, feline, and equine species and food producing animals such as bovine, ovine, porcine and avian species, as well as any other economically important animal (e.g., mink, chinchilla, fox) that is susceptible to intracellular infection. Preferably, the microspheres of the present invention are used to treat humans. The methods are also particularly suitable for treating subjects who are immunocompromised, including human patients diagnosed with acquired immune deficiency syndrome (AIDS) due to infection by human immunodeficiency virus (HIV).

Moreover, the methods and compositions of the present invention can be used with any drug used to treat intracellular infection. Examples of drugs that can be administered by the method of this invention include, but are not limited to, tetracyclines (e.g., doxycycline), roxithromycin, clarithromycin, ofloxacin, josamycin, chloramphenicol, rifampicin (rifampin), cotrimoxazole (trimethoprim/sulfamethoxazole), erythromycin, azithromycin, amoxicillin, streptomycin, ciprofoxacin, cefriaxone, gentamicin, clindamycin clofazimine, amikacin, sparfloxacin and pristinamycin, as well as any other drug or immunomodulator now known or later identified to be effective in treating intracellular infections.

The method of this invention is particularly well adapted to treating tuberculosis, and any drug capable of treating tuberculosis can be administered by the method of this invention. For example, drugs for treating tuberculosis by the process of this invention can include, but are not limited to, the rifamycins (e.g., rifampicin, rifabutin), macrolides, quinolines and any combination thereof, with rifamycins being more preferred and rifampicin or rifabutin being most preferred of the rifamycins.

In most known treatment regimens, tuberculosis is treated with two or more drugs. The present invention can also be used to administer multiple drugs. A combination of one or more microencapsulated drug and one or more of the same or different non-encapsulated drugs could be administered. Moreover, a combination of several microencapsulated drugs could be administered, in the same or different microspheres, and in any combination of large and/or small microspheres.

The methods and compositions of this invention are also particularly well adapted to treating intracellular infection caused by *Mycobacterium avium* and any drug used to treat *Mycobacterium avium* infection can treat *Mycobacterium avium* infection by the methods and with the compositions of this invention. Preferred drugs for treating *Mycobacterium avium* infection include the rifamycins (e.g., rifampicin, rifabutin), clofazimine, ciprofloxacin, parenteral amikacin, sparfloxacin and any combination thereof, rifabutin being most preferred.

The method may further comprise administering a second effective amount of a second suitable drug contained in second biocompatible microspheres that have a diameter of greater than about 10 microns (sometimes "large microspheres"), wherein the second microspheres release the suitable drug at a second effective rate. The second suitable drug may be, but is not necessarily the same as, the first suitable drug. Moreover, the small and/or large microspheres can be administered second and further times. The large microspheres preferably do not exceed 500 microns in diameter, and more preferably do not exceed 150 microns in diameter.

The first and second microspheres can be administered at the same time or different times, and at the same or different locations of the body. The first and second microspheres can also be combined in one composition such as, for example, a blended powder. In addition, free drug can be administered according to treatment protocols for the administration of free drug, as would be well known in the art, in conjunction with the microspheres to complement the treatment. Thus, in another embodiment nonencapsulated drug is administered to the animal in addition to the small microspheres. In still another embodiment nonencapsulated drug is administered to the animal in addition to the large and small microspheres.

The small microspheres can be administered by any method generally known to deliver drug to a cell (e.g., macrophage). The large microspheres can be administered by any method known to deliver drug from the large microspheres to the bloodstream. Methods of administration are generally known in the art and include, for example, administration parenterally (e.g., intravenously (except for large microspheres), by intramuscular injection, by intraperitoneal injection, or subcutaneously), ex vivo, or by oral or nasal inhalation. The small microspheres are preferably administered intravenously, intramuscularly, subcutaneously, orally, or by inhalation, and the large microspheres are preferably administered subcutaneously or intramuscularly. The compositions include an effective amount of the selected drug, and can be in combination with a pharmaceutically acceptable carrier and, in addition, may include other medicinal agents, pharmaceutical agents, carriers, adjuvants, diluents, etc. In some cases, for example, for advanced stages of intracellular infections, it may be advantageous to co-encapsulate one or more drugs in the microspheres.

If ex vivo methods are employed, cells or tissues can be removed and maintained outside the body according to standard protocols well known in the art. The drugs of this invention can be introduced to the cells or tissue via any well known mechanism. The transduced cells can then be infused (e.g., in a pharmaceutically acceptable carrier) or transplanted back into the subject per standard methods for the cell or tissue type. Standard methods are known for transplantation or infusion of various cells into a subject.

In most instances therapy is initiated using two routes of injection, intravenous (small microspheres) and subcutaneous (large microspheres). As one example, small and large microspheres can be injected on Day 1 and followed with a second small microsphere injection on Day 7. Concentrations of drug in the injection would depend upon the particular drug and the amount of drug necessary to achieve blood and urine levels equivalent or greater than the minimal inhibitory concentration (MIC). Because this varies among pathogenic species, it is not possible to state an exact concentration. An exact concentration also cannot be given because injection of microencapsulated drug can be given in conjunction with other antibacterial drugs, either microencapsulated or non-encapsulated. A skilled worker can, however, readily convert any conventional treatment therapy to a microsphere-based therapy of the present invention without undue experimentation, using, for example, the teachings provided in the art, such as those provided in *Remington's Pharmaceutical Sciences.*

The amount of active compound administered, and the relative amounts administered in large microsphere, small microsphere, and nonencapsulated forms, will, of course, depend on the particular disease being treated or prevented, the particular compound or drug being administered, the mode of administration, the species of the subject being treated, the severity of the disease, the overall condition of the subject, the subject's weight and the judgement of the prescribing physician. It is anticipated that the total dose of active compound administered in the treatment regimen of this invention will be no more than, and generally significantly less than, the amount of active compound administered in conventional treatments. The lower dose requirements are due to the targeting effect of delivering the active compound directly to the affected cells and secondly, to the ability of the microspheres to release the active compound over a prolonged period of time, protecting the active compound from enzymatic degradation until it is released either within the cell or into the blood stream. The combination of these attributes of the invention result in the potential to achieve equivalent or superior biological effects with smaller doses of active compounds.

As an example, a total monthly dosage of between about 1 mg/kg and 2,000 mg/kg of body weight of a compound of this invention, preferably between 100 mg/kg and 1,000 mg/kg, encapsulated in the microspheres of this invention can be administered to a subject for which the administration of the compound is indicated, as set forth herein, to treat or prevent an intracellular infection of this invention. The dosage can be divided in any proportion into the small microspheres and large microspheres of this invention and administered by a combination of routes (e.g., intravenous administration of a sufficient amount of small microspheres in one or more administrations to provide 500 mg/kg of compound and subcutaneous administration in one or more administrations of a sufficient amount of large microspheres to provide 500 mg/kg of the compound). The compound-containing microspheres of this invention can be administered once daily or more than once daily. The microspheres can also be administered weekly or monthly and can be administered for an indefinite number of days, weeks or months until it is determined that further administration is not necessary. Such a determination can be made by one of skill in the art by monitoring the subject's signs and symptoms and other clinical parameters associated with the diagnosis of subject's intracellular infection. If it is determined that the intracellular infection has not been adequately treated, has recurred or is likely to recur, the administration of the microspheres of this invention can be resumed. This exemplary treatment regimen is particularly applicable to the treatment of tuberculosis with rifampin.

An added benefit of the invention is that any toxic side effects can be reduced due to lower dose requirements. Thus, in another aspect, the invention provides a method for reducing the toxicity of a drug used to treat intracellular infections comprising encapsulating a first effective amount of a suitable drug in first biocompatible microspheres that have a diameter of from about 1 to about 10 microns, wherein the first microspheres release the suitable drug upon administration at a first effective rate.

In still another aspect the invention provides a method of making a drug formulation having reduced toxicity comprising encapsulating a first effective amount of the suitable drug in first biocompatible microspheres that have a diameter of from about 1 to about 10 microns. The reduction of toxicity can be determined by reference to the level of toxicity of comparable amounts of free drug, as shown further in the Examples provided herein.

The efficacy of administration of a particular dose of a drug in treating intracellular infections in a subject diagnosed as having a disease associated with intracellular infection can be determined by standard methods of evaluation of the particular signs, symptoms and objective laboratory tests for a particular disease, as known in the art. These signs, symptoms and objective laboratory tests will vary depending on the particular disease being treated or prevented as will be well known to any clinician in this field. If 1) a subject's frequency or severity of recurrences is shown to be improved, 2) the progression of the disease is shown to be stabilized, or 3) the need for use of other drugs is reduced, based on a comparison with an appropriate control group and knowledge of the normal progression of disease in the general population or the particular individual, then a particular treatment will be considered efficacious.

Additionally, the efficacy of administration of a particular dose of a drug in preventing an intracellular infection in a subject not known to have a disease associated with an intracellular infection, but known to be at risk of developing a disease associated with an intracellular infection, can be determined by evaluating standard signs, symptoms and objective laboratory tests, as would be known to one of skill in the art, over time. This time interval may be large or small depending upon the particular disease involved. The determination of who would be at risk for the development of a disease such as tuberculosis would be made based on current knowledge of the known risk factors for a particular disease as would be familiar to a clinician in this field, such as exposure to subjects known to be infected by the disease.

Once it is established that disease activity is significantly improved or stabilized by a particular treatment, specific signs, symptoms and laboratory tests will be followed along with a reduced or discontinued treatment schedule. If disease activity recurs, based on standard methods of evaluation of the particular signs, symptoms and objective laboratory tests for a particular disease, treatment can be reinitiated.

The present invention is particularly suited for the treatment of TB-infected patients, whether or not they have developed the disease. Most people that are infected with TB do not develop the disease (~90–95%). Infected people can be diagnosed by a TB skin test and x-ray. The skin test is the definitive marker when determining whether a patient is infected, but a good history is very helpful. To determine whether a patient has the disease, it is necessary to culture the patient's sputum. The definitive diagnosis for the disease is culture and identification of the organism. This can take 3–5 weeks. Generally, 5–10% of infected persons will develop the disease, which, if left untreated can eventually disseminate throughout the body. Time for this progression can vary. Factors that can contribute are health, nutrition, and immune status of the individual. For AIDS patients, progression to death would be more rapid because their immune status has been severely compromised by the HIV.

If TB is diagnosed, the patient is placed upon drug therapy that can last from 6–12 months and typically consists of 2–3 different drugs. Drug therapies using nonencapsulated drug can vary, and are typically revised from year to year. In nonencapsulated drug therapies, a person with an active case of TB is generally treated with more than one drug, such as those shown in Tables A, B, and C, which have been obtained from Friedman, *Tuberculosis: Cent Concepts and Treatment* (1994, CRC Press). Tuberculosis treatment regimens using nonencapsulated drugs are set forth generally in Friedman, *Tuberculosis: Current Concepts and Treatment* (1994, CRC Press). The disclosure of Friedman is hereby incorporated by reference.

Regimens for human administration can also be developed in conjunction with animal studies. These animal studies can be used as models for identifying appropriate human dosing rates (e.g., in mg/kg of body weight) based upon the comparative weight of humans and the animals that are tested (Ji, B., et al., 1993. *Am Rev. Respir. Dis.* 148:1541–1546, incorporated herein by reference).

TABLE A

Dosage recommendation for the initial treatment of tuberculosis in children[a] and adults[b]

| | Dosage | | | | | |
|---|---|---|---|---|---|---|
| | Daily Dose | | Twice Weekly Dose | | Thrice Weekly Dose | |
| Drugs | Children | Adults | Children | Adults | Children | Adults |
| Isoniazid (mg/kg) | 10–20 | 5 | 20–40 | 15 | 20–40 | 15 |
| maximum (mg) | 300 | 300 | 900 | 900 | 900 | 900 |
| Rifampin (mg/kg) | 10–20 | 10 | 10–20 | 10 | 10–20 | 10 |
| maximum (mg) | 600 | 600 | 600 | 600 | 600 | 600 |
| Pyrazinamide (mg/kg) | 15–30 | 15–30 | 50–70 | 50–70 | 50–70 | 50–70 |
| maximum (g) | 2 | 2 | 4 | 4 | 3 | 3 |
| Ethambutol[c] (mg/kg) | 15–25 | 15–25 | 50 | 50 | 25–30 | 25–30 |
| Streptomycin (mg/kg) | 20–40 | 15 | 25–30 | 25–30 | 25–30 | 25–30 |
| maximum (g) | 1.0 | 1.0 | 1.5 | 1.5 | 1.5 | 1.5 |

[a]Children ≦ 12 years of age.
[b]From American Thoracic Society/Centers for Disease Control.
[c]Ethambutol is generally not recommended for children whose visual acuity cannot be monitored (<8 years of age). However, ethambutol should be considered for all children with organisms resistant to other drugs, when susceptibility to ethambutol has been demonstrated, or susceptibility is likely.

TABLE B

Second line antituberculosis drugs[a,b]

| Drug | Dosage Forms | Daily Dose in Children and Adults[c] (mg/kg) | Maximal Daily Dose in Children and Adults (g) | Major Adverse Reactions | Recommended Regular Monitoring |
|---|---|---|---|---|---|
| Capreomycin | Vials: 1 g | 15 to 30 im | 1 | Auditory, vestibular, and renal toxicity | Vestibular function audiometry, blood urea nitrogen, and creatinine |
| Kanamycin | Vials: 75 mg. 500 mg. 1 g | 15 to 30 im | 1 | Auditory and renal toxicity, rare vestibular toxicity | Vestibular function, audiometry, blood urea nitrogen, and creatinine |
| Ethionamide | Tablets: 250 mg | 15–20 p.o. | 1 | Gastrointestinal disturbance, hepatotoxicity, hypersensitivity | Hepatic enzymes |
| ρ-Aminosalicylic acid | Tablets: 500 mg. 1 g delayed release granules Bulk powder | 150 p.o. | 12 | Gastrointestinal disturbance, hypersensitivity, hepatotoxicity, sodium load | Hepatic enzymes |
| Cycloserine | Capsules: 250 mg | 15 to 20 p.o. | 1 | Psychosis, convulsions, rash | Assessment of mental status |

[a]From American Thoracic Society/Centers for Disease Control.
[b]These drugs are more difficult to use than drugs listed in TABLE A. They should be used only when necessary and should be given and monitored by health providers experienced in their use.
[c]Doses based on weight should be adjusted as weight changes.

Table C Current Recommendations For Therapy of Actual or Probable Drug Sensitive Tuberculosis[a] 6Month Therapy Option 1

Eight Weeks of daily isoniazid, rifampin, and pyrazinamide, followed by 16 weeks of isoniazid and rifampin, daily or 2 to 3 times per week. In areas where the isoniazid resistance rate is not documented to be less than 4%, ethambutol or streptomycin should be added to the initial regimen until susceptibility to isoniazid and rifampin is demonstrated. All regimens administered twice or thrice weekly should be monitored by directly observed therapy. A tuberculosis medical expert should be consulted if the patient is symptomatic or smear or culture positive after 3 months.

Option 2

Two weeks of daily isoniazid, rifampin, pyrazinamide, and streptomycin or ethambutol followed by 6 weeks of the same drugs, twice weekly, administered by directly observed therapy, followed by 16 weeks of isoniazid and rifampin administered twice weekly by directly observed therapy in cases where the organism is shown to be drug susceptible. A tuberculosis medical expert should be consulted if the patient is symptomatic or smear or culture positive after 3 months.

Option 3

Thrice weekly isoniazid, rifampin, pyrazinamide, and ethambutol or streptomycin for 6 months, administered by directly observed therapy. (The strongest evidence from clinical trials shows the effectiveness of all four drugs administered for the full 6 months.) There is weaker evidence that streptomycin can be discontinued after 4 months if the isolate is susceptible to all drugs. The evidence for stopping pyrazinamide before the end of 6 months is equivocal for the thrice weekly regimen, and there is no evidence for the effectiveness of this regimen with ethambutol for less than the full 6 months. A tuberculosis medical expert should be consulted if the patient is asymptomatic or smear or culture positive after 3 months.

HIV-Related Tuberculosis

Option 1, 2, or 3 under 6-month therapy can be used, but patients should be followed much more closely. If there is any problem with response to treatment, the usual evaluation should ensue, and therapy may be prolonged.

9-Month Therapy

Nine months of daily isoniazid and rifampin, or 1 to 2 months of daily isoniazid and rifampin followed by 7 to 8 months of daily or twice weekly isoniazid and rifampin for a total of 9 months of therapy. Directly observed therapy should be used for twice weekly administration. Ethambutol or streptomycin should be added for the first 2 months in areas where the isoniazid resistance rate is not documented to be less than 4%.

4-Month Therapy

Treat as per options 1, 2, or 3 under 6-Month therapy, truncated after 4 months in patients who are not at high risk and have smear-negative, culture-negative pulmonary tuberculosis.

[a]Adapted from American Thoracic Society/Centers for Disease Control.

Patients who are being treated for TB are generally seen every month to observe their response to treatment. Sputum cultures are taken until they convert to negative. It is recommended that this be done every week. Patients are also encouraged to continue their therapy, but this is sometimes very difficult because the patients may actually feel better if they stop taking the drug. This is because of some of the side effects produced by the drugs. Physicians can also monitor clinical parameters as liver functions tests (i.e., enzymes), blood count, blood urea nitrogen, creatinine, etc., to ensure that no toxicity has developed to the drugs. If toxicity develops, the regimen can be modified. Therapy is generally considered successful by observing continued negative sputum cultures. However, TB can develop into what is referred to as the "dormant state." This is not completely understood but involves the ability of the tubercle bacilli to cease to grow and remain dormant for long periods. In some cases, a person can have this state for many years, even if he or she has been treated. Even though the patient's cultures are negative, the patient still remains infected. As that person gets older and his or her immune system becomes less efficient, he or she can develop a reactivated case of TB.

If a person is only skin test positive for TB and shows no signs of active disease (e.g., negative sputum), it is possible to treat him or her with only one drug (chemoprophylaxis). In that case isoniazid can be used. As shown in Table D, this is also complicated and varies depending on a variety of factors. Generally the time frame is 6–12 months.

TABLE D

| | Infection and treatment[a] | |
|---|---|---|
| Induration | Groups in Whom Infection Is Presumed to Be Present at the Specified Degree of Induration | Treatment[b] |
| <5 mm | Adolescents and children who are close contacts | Treat until 12 weeks after last exposure, at which time skin test is repeated |
| ≧5 mm | Close contacts | Treat all ages for 6–12 months |
| | HIV+, or unknown status at risk | Treat all ages for 12 months |
| | Upper lobe fibrotic lesion | Treat all ages for 12 months if not previously treated. Four months of multidrug chemotherapy also is acceptable |
| ≧10 mm | Silicosis | Treat all ages for 12 months if not previously treated. Four months of multidrug chemotherapy also is acceptable |
| | High incidence or risk to others | Treat age <35 for 6–12 months |
| | IVDA (HIV negative) | Treat all ages for 6–12 months |
| | Medical risk | Treat all ages for 6–12 months |

TABLE D-continued

| Induration | Groups in Whom Infection Is Presumed to Be Present at the Specified Degree of Induration | Treatment[b] |
|---|---|---|
| | Infection and treatment[a] | |
| | | (12 months in persons who are immunocompromised) |
| ≧15 mm[c] | Low risk | Treat age <35 for 6–12 months |
| 10 mm increase over a 2-year period for age <35, or skin test induration ≧10 mm in a person <4 years of age, regardless of previous test results | Recent converter | Treat for 6–12 months; treat for 9 months in infants and children |
| 15 mm increase over a 2-year period for age ≧35[c] | Recent converter | Treat for 6–12 months |

[a]Adapted from American Thoracic Society, Centers for disease Control, and American Thoracic Society/ Centers for Disease Control
[b]Isoniazid 300 mg per day, or 15 mg/kn, up to 900 mg, twice weekly.
[c]The degree of induration that is accepted as a positive result may be modified based on regional factors such as the risk of atypical mycobacterial infections and the risk of actual tuberculous infection. In areas where the risk of actual tuberculous infection far exceeds the risk of atypical infection, such as New York City, the degree of induration that is accepted as positive should be 10 mm.

Pharmaceutically administrable compositions can be prepared by several methods including, for example, dispersing active microspheres as described herein and optional pharmaceutical adjuvants in an excipient, such as, for example, water, saline aqueous dextrose, glycerol, ethanol, and the like, to thereby form a suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art as described, for example, in *Remington's Pharmaceutical Sciences.*

The compositions of the invention may be readily synthesized using techniques generally known to microsphere and microparticle formulators. Suitable experimental methods for making microspheres and microparticles are described, for example, in U.S. Pat. No. 5,407,609 to Tice, et al., and U.S. Pat. No. 5,654,008 to Herbert et al., the disclosures of which are hereby incorporated by reference for their general teachings and for their synthesis teachings. Methods for making specific and preferred compositions of the present invention are described in detail in the Examples below.

Suitable materials with which to prepare the microcapsules include, but are not limited to: poly(dienes) such as poly(butadiene) and the like; poly(alkenes) such as polyethylene, polypropylene, and the like; poly(acrylics) such as poly(acrylic acid) and the like; poly(methacrylics) such as poly(methyl methacrylate), poly(hydroxyethyl methacrylate), and the like; poly(vinyl ethers); poly(vinyl alcohols); poly(vinyl ketones); poly(vinyl halides) such as poly(vinyl chloride) and the like; poly(vinyl nitriles); poly(vinyl esters) such as poly(vinyl acetate) and the like; poly(vinyl pyridines) such as poly(2-vinyl pyridine), poly(5-methyl-2-vinyl pyridine) and the like; poly(styrenes); poly(carbonates); poly(esters); poly(orthoesters); poly(esteramides); poly(anhydrides); poly(urethanes); poly(amides); poly(lactide); poly(glycolide); poly(caprolactone); poly(hydroxybutyrate); cellulose ethers such as methyl cellulose, hydroxy ethyl cellulose, hydroxypropyl methyl cellulose, and the like; cellulose esters such as cellulose acetate, cellulose acetate phthalate, cellulose acetate butyrate, and the like; poly(saccharides), proteins, gelatin, starch, gums, resins, and the like. These materials may be used alone, as physical mixtures (blends), or as copolymers. A preferred group of materials include biodegradable polymers including but not limited to poly(lactide-co-glycolide), poly(lactide), poly (lactide-co-caprolactone), poly(caprolactone), and poly(anhydride).

Thus, to accomplish the objects of the present invention, there is also provided a composition for treating an intracellular infection in an animal comprising an effective amount of a suitable drug contained within biocompatible microspheres, wherein the microspheres have a diameter from about 1 to about 10 microns (a/k/a small microspheres), and release the suitable drug upon administration at an effective rate. The composition is particularly well suited for treating tuberculosis and an *M. avium* infection.

In the case of compositions for treating tuberculosis, the drug preferably is a rifamycin, a macrolide, a quinoline, or a combination thereof, and more preferably is a rifamycin, which most preferably is rifampicin or rifabutin. The biocompatible microspheres may also comprise a pharmaceutical carrier which, preferably, is for intravenous administration.

In certain embodiments the invention provides the second large microspheres discussed previously in addition to the small microspheres. Thus, in still another embodiment the invention provides a kit for treating an intracellular infection in a patient comprising (a) an effective amount of a suitable drug contained within first biocompatible microspheres (a/k/a small microspheres) that release the suitable drug upon administration at a first effective rate, and (b) an effective amount of a suitable drug contained within second biocompatible microspheres (a/k/a/large microspheres) that release the suitable drug upon administration at a second effective rate, wherein the first microspheres have a diameter from about 1 to about 10 microns, and the second microspheres have a diameter greater than about 10 microns, and wherein the drug may be the same or different for the first and second microspheres.

In even another embodiment the invention provides a kit for treating an intracellular infection in an animal comprising (a) an effective amount of a suitable drug contained within first biocompatible microspheres that release the suitable drug upon administration at a first effective rate, and (b) an effective amount of a suitable nonencapsulated drug, wherein the first microspheres have a diameter from about 1 to about 10 microns, and wherein the drug may be the same or different for the first microspheres and nonencapsulated drug.

The large microspheres of this invention preferably impart continuing and prolonged systemic release of the drug to the patient. In contrast, the small microspheres preferably are designed to delay release of drug until uptake by the macrophage.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in degrees centigrade (° C.) or is at room temperature, and pressure is at or near atmospheric.

Example 1

In vitro Studies

Preparation of Small Sized (1–10 μm) Rifampicin Microspheres

Small microspheres were prepared as follows: First an excipient solution was prepared by dissolving approximately 2.8 g of poly (DL-lactide-co-glycolide) (DL-PLG) in 11.0 g of either methylene chloride or ethyl acetate. To this excipient solution, approximately 150 mg of rifampicin was added and a homogeneous solution obtained by thorough mixing. The resulting mixture was then introduced into 300 ml of an aqueous process medium containing poly(vinyl alcohol) (PVA) (Air Products Inc., Allentown, Pa.) and carboxymethyl cellulose (CMC) (Air Products Inc., Allentown, Pa.) (2.0 wt. % PVA/0.5 wt. % CMC). The solution was stirred for 20+/−10 seconds with the aid of a Silverson emulsifier (Silverson Machines, East Longmeadow, Mass.) to yield an emulsion consisting of appropriately sized microdroplets. The emulsion was then immediately transferred to 5.0 liters of water. The resulting microspheres were then concentrated by centrifugation, collected and lyophilized. The rifampicin content of each lot of mnicrospheres was determined by extracting the rifampicin from a known quantity of microspheres and quantifying the amount of rifampicin spectrophotometrically.

In vitro Release Analysis of Rifampicin Microspheres

To assess the release kinetics of rifampicin from the microspheres, multiple samples of each microsphere lot were weighed into 16-X 100-mm glass test tubes equipped with serum separators (Fisher Scientific). To each tube, 3.0 ml of receiving fluid consisting of 0.05 M sodium phosphate solution was added. The test tubes were placed in an incubator maintained at 37° C. The receiving fluid was removed and replaced with new fluid at 2, 6, 24 h, and every 24 to 48 h thereafter. The amount of rifampicin released was determined by a standard HPLC assay described in the U.S. Pharmacopeia. An absorption maximum of 254 nm was used.

Microsphere Size Determination and Sterilization

The size distribution for each lot of rifampicin microspheres was determined using a Malvern Particle Size Analyzer (Malvern Instruments, Malvern, UK). The microsphere lots were sterilized by gamma radiation (25 kGy dose) by Neutron Products Inc., Dickerson, Md. Following sterilization, microsphere formulations were stored desiccated at −20° C. until use. Surface morphology of microsphere formulations was examined by scanning electron microscopy (SEM).

Mycobacterial Strains

*Mycobacterium tuberculosis* H37Rv (ATCC 27294, SRI #1345) was maintained on Middlebrook 7H1O agar slants, containing 0.5% glycerol and 10% OADC (Difco). The minimal inhibitory concentration (MIC) for rifampicin was determined by Etest to be 0.06–0.25 μg/ml.

Monocyte Cell Lines

The J774 murine macrophage cell line was obtained from the American Type Culture Collection (ATCC TIB 67; Rockville, Md.) and maintained in RPMI 1640 medium supplemented with 10% heat-inactivated fetal calf serum and 2 mM L-glutamine. The Mono Mac 6 cell line (MM6) was obtained from the German Collection of Microorganisms and Cell Cultures, Braunschweig, Germany. MM6 cells were maintained in RPMI-1640 containing 10% (vol/vol) fetal calf serum, 2 mM L-glutamine, non-essential amino acids, 1 mM sodium pyruvic acid, and 9 g of bovine insulin (Sigma Chem. Co., St. Louis, Mo.) per ml. Cell lines were routinely assayed to verify absence of mycoplasma contamination using the Gen-Probe Mycoplasma Rapid Detection System (Gen-Probe, San Diego, Calif.).

Treatment of Monocytes With Microspberes

The J774 and MM6 monocytic cell lines were treated with either placebos (i.e. microspheres without drug, only polymeric excipient) or rifampicin loaded microsphere formulations, using the procedure described below. In one set of experiments, non-infected monocytes were used in order to obtain uptake of microspheres and release of rifampicin from microspheres. In another set of experiments, *M. tuberculosis* H37Rv-infected monocytes were used in order to examine the intracellular effectiveness of rifampicin-loaded microsphere formulations. In additional experiments, J774 macrophages were allowed to take up rifampicin-loaded microspheres for 24 hours; the amount of drug delivered during that uptake period was assessed. That information was then used to compare the effectiveness of rifampicin given in microsphere formulations with equivalent concentrations of free drug used to treat *M tuberculosis*—infected macrophages.

Mono Mac 6 cells were plated in 12-well tissue culture plates (Corning) at a concentration of $4\times10^5$ cells/ml/well in MM6 medium containing 1% FBS. Three plates for each formulation were set up to harvest at 2, 4, and 7 days. To nine wells per plate, 40 μg of rifampicin containing microspheres were added; three wells per plate were controls. At time of harvest, the contents of each well were transferred to sterile macrophage tubes and centrifuged at 10,000 g for four minutes at 4° C. Supernatants from triplicate wells were removed and transferred to a sterile 12-X 100-mm PYREX tube, frozen and lyophilized. Microscopic observation of supernatants showed absence of macrophages or microspheres.

The J774 macrophages were plated in Falcon 12-well tissue culture plates at a concentration of $2\times10^5$ cells/well/ml. At 24 hours, the medium was replaced with 1.0 ml medium per well containing only 1% FBS. Experimental wells had 40 μg of microspheres added. Samples were harvested at 2, 4 and 7 days in the same manner as MM6 samples. For bioassay, lyophilized samples were resuspended in 240 μl sterile water (Sigma) and kept on ice. Eighty-microliter samples from each pyrex tube, equivalent to the contents of one well of a triplicate, were absorbed onto disks and evaluated for drug activity using the bioassay described below.

Macrophage Viability Assays

Cell viability was determined by means of a modified MTT (3-[4,5-dimethylthiazol-2-yl]-2,5-diphenyltetrazolium bromide [Thiazolyl Blue]) Cytotoxicity Assay (Sigma).

Bioassay

A bioassay, using *Staphylococcus aureus* (ATCC 29213) was developed to determine rifampicin concentrations in macrophage culture supernatants. Stock solutions of rifampicin in HPLC grade methanol (Fisher) were prepared, aliquoted and frozen at −70° C. For assay, standard solutions of rifampicin, in the appropriate macrophage cell line's tissue culture medium, were prepared in duplicate and assayed with test samples to provide a standard concentration curve.

Sterile filter paper disks (13 mm in diameter, Schleicher and Schuell) were aseptically placed into individually coded wells of 12-well tissue culture plates and 80 μl of each sample was absorbed onto the disc. During preparation, plates were placed upon cold pack trays. The tissue culture plates containing impregnated disks were refrigerated at 4° C. until application onto agar plates. Using the direct colony suspension method (NCCLS, Document M2-A5, vol. 13, #24, 1993), a suspension of *Staphylococcus aureus* (ATCC 29213) was prepared and adjusted to match a 0.5 McFarland turbidity standard. Within 15 minutes of suspension preparation, 150-mm Mueller Hinton agar plates were swabbed for lawn growth. The previously loaded disks of macrophage culture supernatants, as well as standard drug concentrations, were aseptically applied to the inoculated plates using sterile forceps and gently tapped to make uniform contact with the medium. Plates were sealed with parafilm, inverted, and placed in a 37° C. incubator (no $CO_2$) for 18–20 h. At termination of incubation, zones for drug standards were measured and a standard curve plotted. Zone diameters for test samples were measured and values entered into the computer for regression analysis to determine the amount of drug in 80 μl of macrophage culture supernatant. The value was converted to μg of drug per ml of macrophage culture supernatant.

Determination of Rifampicin Content in Phagocytosed Microspheres

J774 macrophages were plated at a concentration of $2\times10^5$ cells/ml/well and placed in a $CO_2$ incubator at 37° C. Cells were incubated overnight, after which medium was replaced with medium containing 1% serum. After an additional incubation of 24 hours, one set of macrophages (one 12-well plate) was dosed with 150 μg of microspheres comprising 1.4 wt. % rifampicin, a second set (one 12-well plate) was dosed with 150 μg of placebo microspheres, and a third set (one 12-well plate) maintained as a reagent control. After incubation at 37° C. for 24 hours, adherent macrophages were washed three times to remove unphagocytosed microspheres (as evidenced by microscopic observation). Three hundred microliters of sterile 0.125% SDS in water (Sigma) was added to each well and plates shaken briefly by hand. Following incubation at 37° C. for 20 minutes, the contents of four wells were pooled in sterile PYREX screw-cap tubes. Wells were washed three times with sterile water (Sigma) which was added to the tubes. This resulted in three pooled samples per plate. Samples were frozen and lyophilized.

Following lyophilization, 400 microliters of ethyl acetate (certified, A.C.S., Fisher) was added to each tube and the tubes were shaken overnight. Ethyl acetate dissolves the microsphere polymer and releases free rifampicin. Tubes were then placed in a desiccator and the atmosphere evacuated with a vacuum pump for six hours. Samples were then reconstituted in 320 μl of J774 medium containing 1% serum and the rifampicin bioassay performed as described above.

Preparation of Mycobacteria for Infection

Before infection of monocyte cell lines, *Mycobacterium tuberculosis* H37Rv was initially grown in Middlebrook 7H9 (Difco Laboratories, Detroit, Mich.) containing 0.5% Tween 80 (Sigma) and 10% albumin-dextrose-catalase (ADC) (Difco). After the mycobacteria had reached exponential phase, they were dispersed by vortexing with glass beads and clumps allowed to settle for 30 min. Supernatant was removed, aliquoted, frozen at −70° C., and then thawed and used for infection by resuspension in appropriate cell culture medium. Actual CFUs/ml were determined by preparation of serial dilutions in Dulbecco's PBS (DPBS, Mediatech, Inc., Hemdon, Va.) and plating on 7H10 agar.

Infection of Monocytes

Prior to infection, J774 cells were plated at a concentration of $2\times10^5$ cells per ml per well in 12-well tissue culture dishes (Falcon). After allowing cells to adhere overnight, the medium was replaced with fresh medium containing 1% serum in order to reduce cell proliferation. After 48 h, the adherent cells were enumerated by means of an ocular grid to determine the number of macrophages. Mycobacteria were suspended in RPMI-1640 containing 1% fetal bovine serum, and the suspension was dispensed into individual wells at a density of 5 mycobacteria per macrophage. Infected J774 cells were then incubated at 37° C. in an atmosphere containing 5% carbon dioxide for 4 h. Following incubation, the supernatant was aspirated, and the cells washed two times with DPBS (Mediatech) to remove unphagocytosed mycobacteria. Fresh medium (1.0 ml), with or without microsphere preparations, or free rifampicin, were then added to each well, and experiments continued to completion. One milliliter of fresh medium was added at day 4.

Before infection, MM6 cells were adjusted to $8\times10^5$ cells per ml, and 0.5 ml per well was dispensed in 12-well tissue culture dishes (Corning Costar Corp., Cambridge, Mass.). The mycobacteria were then added to the MM6 cells to achieve a final ratio of 20 mycobacteria per macrophage, with a density of $4\times10^5$ MM6 per 1.0 ml per well. After infection for 4 h, the infected MM6 cells were collected by centrifugation (200×g ) and washed twice with Dulbecco's phosphate-buffered saline (DPBS, Mediatech) to remove any unphagocytosed mycobacteria. The cells were then replated at a density of $4\times10^5$ cells per 1.0 ml per well, with appropriate wells containing microsphere preparations, and the plates were incubated at 37° C. with 5% carbon dioxide. One milliliter of fresh medium was added at day 4, and infection continued until CFU assay.

Determination of CFU

Determination of CFU at zero hour was conducted by first lysing the monocytes with 0.25% (wt/vol) sodium dodecyl sulfate (SDS) in DPBS, then plating serial dilutions onto 7H1O agar plates. As a means of decreasing viscosity, 5 μl (5 U of activity) of RQ DNase (Promega Corp. Madison, Wis.), with $MgSO_4$ (5 mM), was added to each well following addition of SDS, and plates were incubated at 37° C. for 20 minutes. The plating procedure was repeated at 7 days and CFU enumerated after 10–14 days incubation of cultures.

Results of Example 1

Characteristics of Microsphere Formulations

Representative rifampicin-loaded microspheres are described in Table 1. Formulations 5 and 6 were selected for further studies.

TABLE 1

Representative formulations of rifampicin-loaded microspheres.

| Formulation Number | Excipient | Excipient Solvent | Rifampicin Content, wt % Theoretical | / Observed | Microsphere Size, μm[a] | In vitro Release (%) after 2 days |
|---|---|---|---|---|---|---|
| 1 | 60:40 DL-PLG | Methylene Chloride | 2 | 0.62 | 15 | 0 |
| 2 | 60:40 DL-PLG | Ethyl Acetate | 5 | 0.25 | 8.3 | 5 |
| 3 | 60:40 DL-PLG | Methylene Chloride | 5 | 3.1 | 10 | 2 |
| 4 | 60:40 DL-PLG | Methylene Chloride | 5 | 2.9 | 8.9 | 3.8 |
| 5 | 60:40/50:50 DL-PLG[b] | Methylene Chloride | 5 | 1.4 | 7.5 | 8.0 |
| 6 | 60:40/50:50 DL-PLG[b] | Methylene Chloride | 5 | 1.8 | 8.8 | 7.0 |
| 7 | 60:40/50:50 DL-PLG[b] | Methylene Chloride/CMC[c] | 5 | 3.2 | 14.7 | NA |

[a]Data reported as 90 volume percentiles.
[b]Excipient is a blend of 60:40 DL-PLG and low molecular weight 50:50 DL-PLG (i.v. 0.23 dL/g).
[c]CMC: sodium carboxymethylcellulose was used as a surfactant. All others PVA was used as the surfactant.

In vitro Release of Microspbere Formulations

Initially, rifampicin-loaded microsphere formulations were evaluated for in vitro release at 2 days. Based upon this information and other characteristics, including rifampicin content and microsphere size, formulations were then chosen for extended in vitro release evaluation (Table 1). To conform to the seven day macrophage experiments, extended release was evaluated for six days. Formulations 4, 5, and 6 were chosen for these extended studies, which are given in FIG. 1. Formulations 5 and 6 produced the best in vitro release pattern, resulting in 21 and 12% cumulative in vitro drug release, respectively, after six days (FIG. 1).

Microsphere Size Distribution and Surface Morphology

Figure 2A:
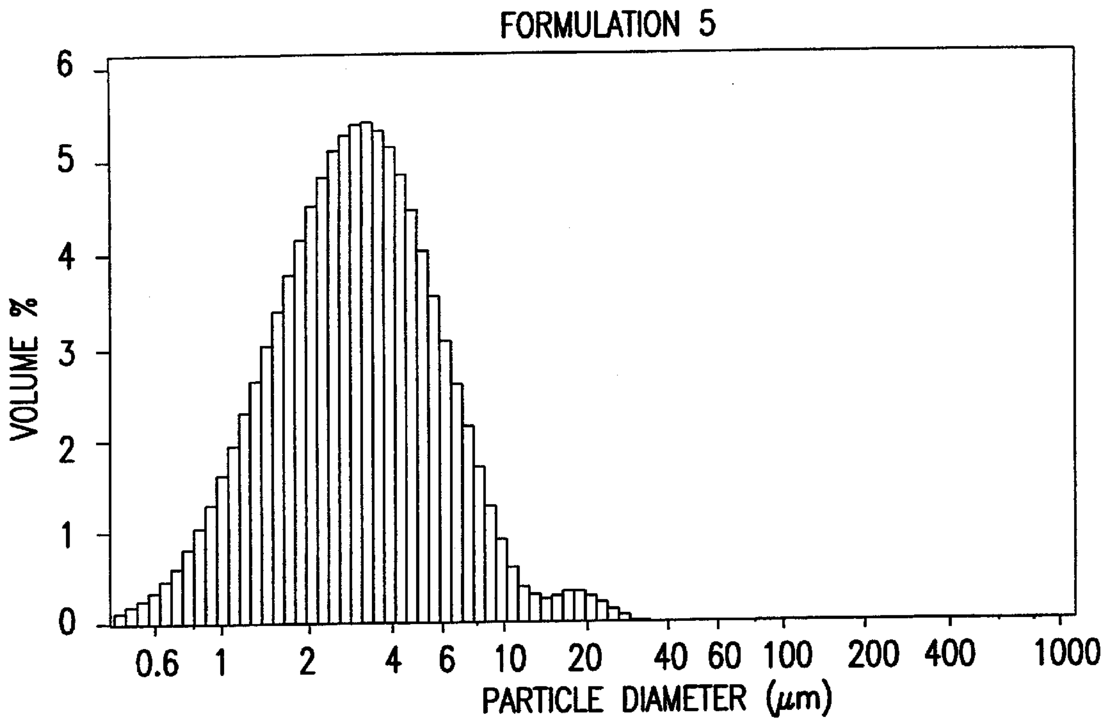
FIGS. 2A and 2B show the size distribution of rifampicin-loaded microsphere Formulations 5 and 6 respectively from Example 1 as determined with a Malvern particle size analyzer.
Figure 2B:
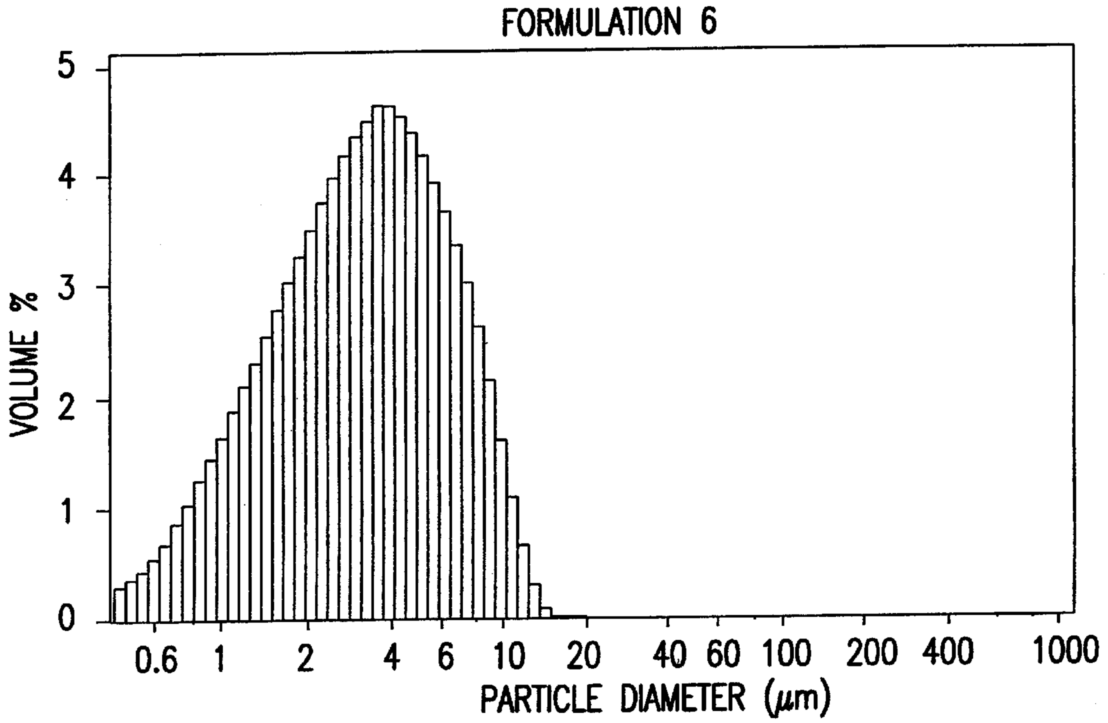
Figure 3A:
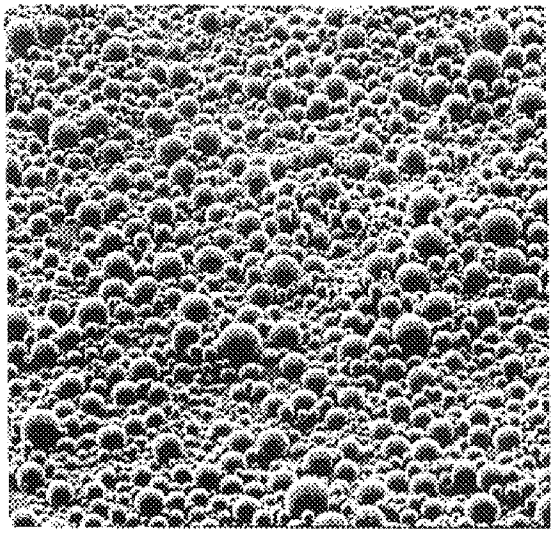
FIGS. 3A and 3B show scanning electron micrographs of rifampicin-loaded microsphere Formulation 5 of Example 1. Bars represent 10 micrometers.
Figure 3B:
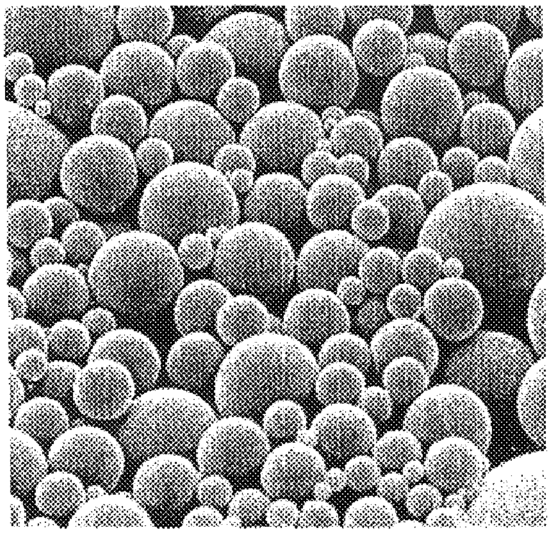

Each microsphere formulation was evaluated for size distribution and surface morphology to ensure optimum delivery characteristics to macrophages. Size distribution for Formulations 5 and 6 are given in FIGS. 2A and 2B. Surface morphology of microsphere Formulation 5 is shown in FIGS. 3A and 3B.

Release of Rifampicin From Macrophages Treated With Various Microsphere Formulations Before experiments were conducted to determine effectiveness of rifampicin-loaded microspheres on intracellularly replicating mycobacteria, it was necessary to determine release characteristics of microsphere formulations within macrophages. Three formulations were chosen for this purpose, Formulations 5, 6, and 7 (Table 2). Each of these formulations are described in Table 1.

Of the three formulations, Formulation 5 gave the best release pattern in both the MM6 and J774 monocytic cell lines (Table 2). At the end of seven days, release from this formulation resulted in approximately 2.6 and 8.1 times greater concentration of rifampicin in the MM6 than Formulations 6 and 7, respectively (Table 2). In the J774, release from Formulation 5 was 2.7 and 1.5 times greater than Formulations 6 and 7, respectively, at the end of seven days (Table 2). For this reason, Formulation 5 was chosen for more extensive studies in macrophages.

TABLE 2

Release characteristics of rifampicin-loaded microsphere formulations in MM6 and J774 monocytic cell lines. Experiments were conducted for 7 days. Rifampicin concentrations in cell supernatants were quantitated by means of a bioassay. Each experiment was conducted in triplicate and is reported as the mean ± standard error of the mean (SEM).

| Time (Days) | MM6 Formulation 5 (μg RIF/ml) | MM6 Formation 6 (μg RIF/ml) | MM6 Formulation 7 (μg RIF/ml) | J774 Formulation 5 (μg RIF/ml) | J774 Formulation 6 (μg RIF/ml) | J774 Formulation 7 (μg RIF/ml) |
|---|---|---|---|---|---|---|
| 2 | <0.008[1] | <0.008[1] | <0.008 | 0.026 ± 0.006 | <0.008 | <0.008[1] |
| 4 | 0.037.± 0.005 | 0.0011 ± 0.0 | 0.009 ± .0002 | 0.026 ± 0.004 | 0.0084 ± 0.0006 | 0.0097 ± 0.0008 |
| 7 | 0.044 ± 0.001 | 0.017 ± 0.002 | 0.0054 ± 0.001 | 0.040 ± 0.005 | 0.015 ± 0.001 | 0.026 ± 0.002 |

[1]Detectable level of the bioassay is 0.008 μg/ml.

Macrophage Viability Assays

To assess effects of microsphere formulations on macrophages, viability assays were conducted with the MM6 human monocytic cell line. The effect of free drug, and equivalent drug delivered with microspheres, on macrophage viability is given in Table 3. The MIC for the *M. tuberculosis* H37Rv strain used in this investigation is 0.06–0.25 μ/ml. Three doses were tested based upon the higher MIC value, and were 0.25, 0.75, and 2.0 μg/ml. For treatment with microsphere formulations, equivalent doses were used, based upon the loading percent for that particular formulation. In this case, the formulation contained 1.4 wt. % of rifampicin (Formulation 5, see above), therefore 18, 54, and 143 μg of the microsphere formulation were necessary to deliver sufficient rifampicin for MIC, three times MIC (3×MIC), and eight times MIC (8×MIC) concentrations, respectively (Table 3).

TABLE 3

Effect of rifampicin-loaded microspheres on viability of macrophages at the end of a seven day dosing. Microsphere Formulation 5 (1.4 wt % rifampicin) was used in these experiments.

| Factor | Amount of Rifampicin (μg/ml) | Effect on MM6 (% Viability after 7 days) | Amount of microspheres necessary to deliver equivalent concentration of rifampicin (μg/ml) | Effect on MM6 (% Viability after 7 days) |
|---|---|---|---|---|
| MIC | 0.25 | 91 | 18 | 100 |
| 3X MIC | 0.75 | 77 | 54 | 100 |
| 8X MIC | 2.0 | 42 | 143 | 92 |

In preliminary experiments (data not presented), the lower end of the MIC range (0.06 μg/ml) was used for rifampicin-loaded microspheres. However, because of percent release from microspheres during the experimental time period, reduction in mycobacterial intracellular growth was observed but it was not significant. With higher MIC equivalents presented in Table 3, it was possible to obtain significant reductions in mycobacterial growth with the microsphere formulations (see FIG. 4). At these concentrations it was observed that rifampicin, delivered by microspheres, had reduced toxicity as compared to rifampicin delivered at equivalent concentrations extracellularly (Table 3).

Effectivenes of Rifampicin-loaded Microspheres on Intracellular Growth of *M. tuberculosis*

The antimycobacterial effectiveness of rifampicin-loaded microspheres was examined in both the murine J774 and human MM6 monocytic cells lines. Following infections of monocytic cell lines with *M. tuberculosis* H37Rv, cells were treated with either rifampicin, added directly to culture medium or by means of drug-loaded microspheres. Infected cells were treated with rifampicin concentrations equal to the MIC (i.e., 0.25 μg rifampicin/ml) and three and eight times the MIC concentration (i.e., 0.75 and 2.0 μg rifampicin/ml, respectively) (FIG. 4).

Figure 4A:
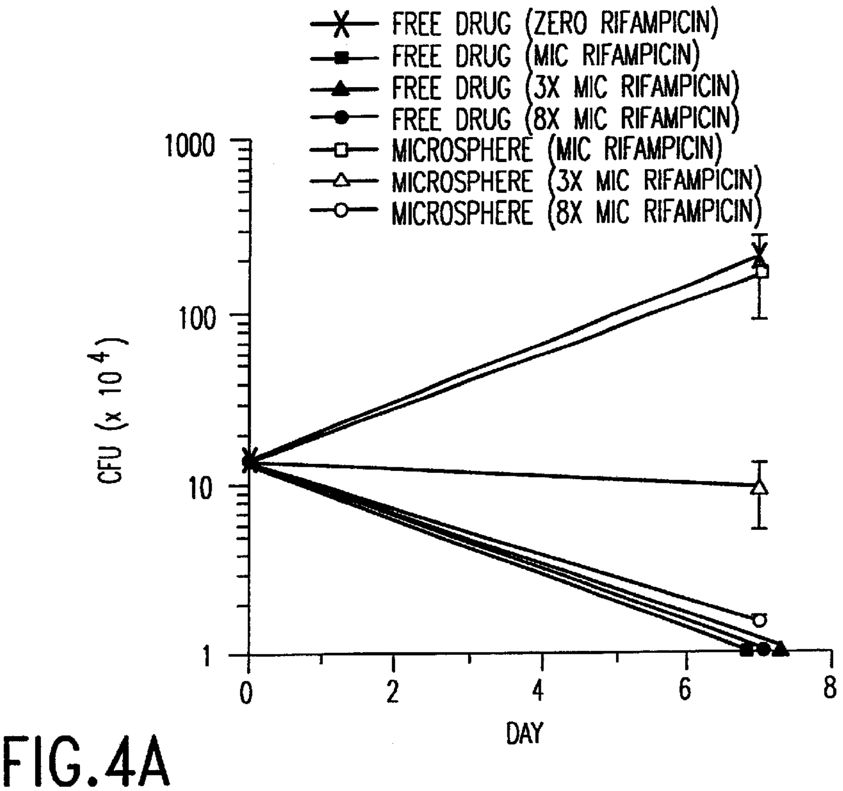
FIGS. 4A and 4B show the effectiveness of rifampicin-loaded microsphere Formulation 5 of Example 1 at reducing intracellular growth of *M. tuberculosis* H37Rv in murine J774 and human MM6 monocytic cell lines respectively.
Figure 4B:
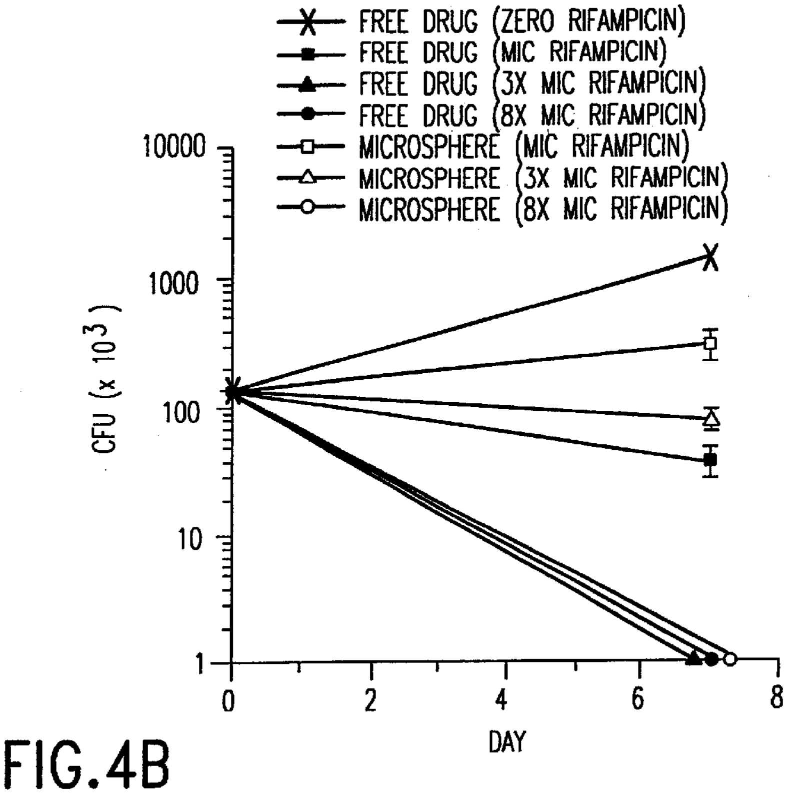

In the J774 murine cell line, significant reduction in CFUs (P<0.001) was observed for all three concentrations of rifampicin given as free drug (FIG. 4A). For rifampicin delivered in microsphere Formulation 5 (1.4 wt. %), the 3×MIC and 8×MIC concentrations both resulted in significant reductions in CFUs (P<0.001) at seven days (FIG. 4A). The rifampicin-loaded microspheres, given at a concentration equivalent to the MIC (i.e., 0.25 μg/ml), did not cause significant reduction in CFUs at seven days (FIG. 4A). However, as extrapolated from data presented in Table 2, only 8% of the rifampicin had released from the microsphere formulations by day seven. Even so, significant reduction of CFUs was observed with 3×MIC and 8×MIC equivalent rifampicin-loaded microspheres. With the MM6 cell line, significant reduction of CFUs was observed for all concentrations of free rifampicin (P<0.001) as well as equivalent concentrations of rifampicin-loaded microspheres (P<0.05<0.001, and <0.001, for MIC, 3×MIC and 8×MIC, respectively) (FIG. 4B).

Effectiveness of Drug Delivery by Microspheres Versus Free Drug

Figure 5A:
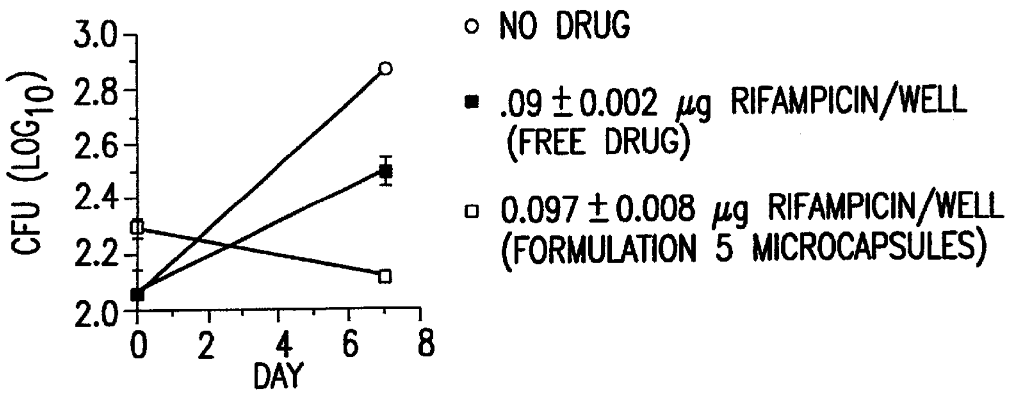
FIGS. 5A–5C show a comparison of antimycobacterial effectiveness of free-rifampicin versus equivalent doses delivered with rifampicin-loaded microspheres, according to the procedure of Example 1.
Figure 5B:
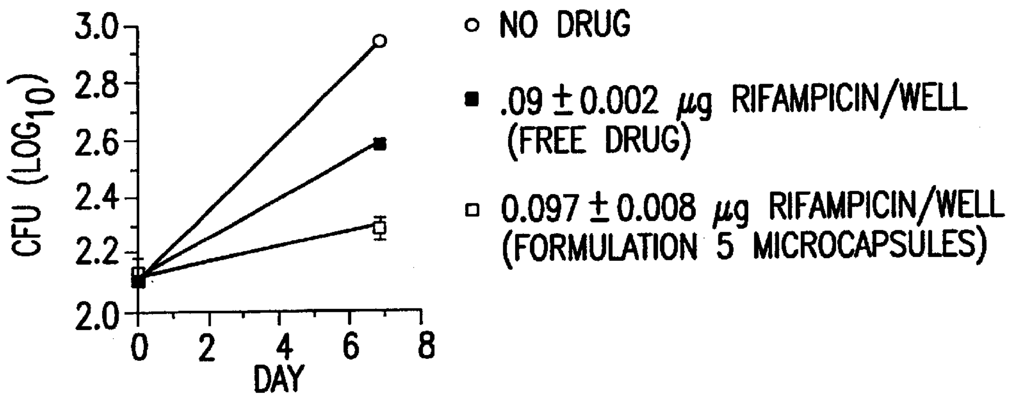
Figure 5C:
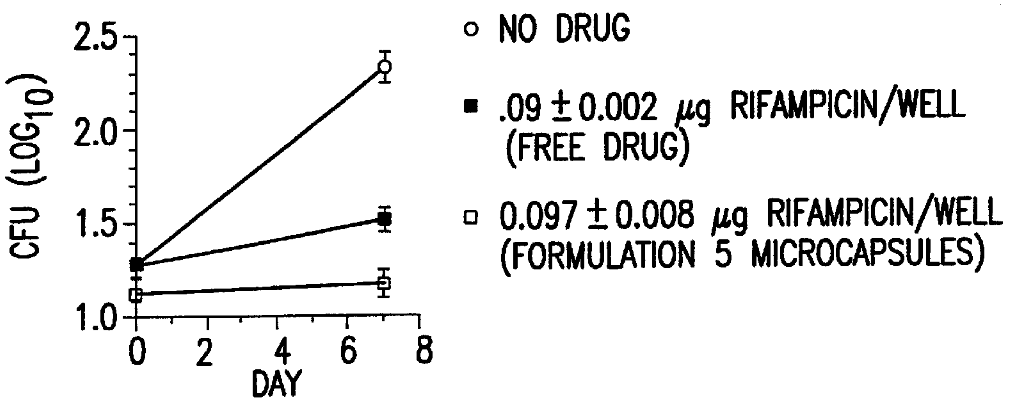

Several experiments were conducted in order to (1) determine the amount of rifampicin that is delivered to macrophages with microspheres following 24 h feeding prior to infection and (2) compare the effectiveness of that dose to an equivalent dose of free drug. The J774 murine macrophage cell line was first allowed to phagocytose rifampicin-loaded microspheres (Formulation 5, 1.4 wt. % rifampicin) for 24 hours. Using the bioassay, the mean concentration of rifampicin that was delivered with the microspheres was determined to be 0.094±0.003 μg/well (n=9). This information was then used to set up three successive experiments, in triplicate, to compare the effectiveness of equivalent doses of rifampicin given extracellularly. In each group, J774 cells were infected with *M. tuberculosis* H37Rv and either not treated, treated with free rifampicin, or treated with rifampicin-loaded microsphere Formulation 5. The experimental data for all three experiments is given in FIGS. 5A–C. The mean free drug concentration used to treat infected macrophages was 0.09±0.002 μg rifampicin/well (n=9) and the mean concentration of rifampicin delivered by total release from microspheres was 0.097±0.008 mg/well (n=9). In each experiment, doses of rifampicin delivered by means of the microsphere formulation were able to significantly reduce CFUs as compared to the nontreated control (P was determined to be ≦0.001 for each experiment) (FIGS. 5A–C). More importantly, doses of rifampicin delivered by microspheres were able to significantly reduce CFUs as compared to equivalent doses delivered as free drug (P was determined to be ≦0.001 for each experiment) (FIGS. 5A–C).

Example 2

In vivo Mouse Studies

Preparation of Large (>10 micron) Microspheres for Extended-Release of Rifampicin The process used to prepare large microspheres, designed to release rifampicin over time, was very similar to the process used to make the small microspheres described in Example 1. An excipient solution was prepared by dissolving 4.0 g DL-PLG in 16.0 g of an organic solvent, in this case, methylene chloride or ethyl acetate. Approximately 1 g of rifampicin was introduced into the excipient solution and again a homogeneous solution was obtained after thorough mixing for 20+/−10 seconds. The rifampicin/DL-PLG solution was introduced into an aqueous process medium consisting of 2.0 wt % PVA. An emulsion was formed using a standard laboratory mixer and again transferred into 5.0 liters of water. The resulting microspheres were collected over standard ASTM mesh sieves (Fisher Scientific).

Figure 6:
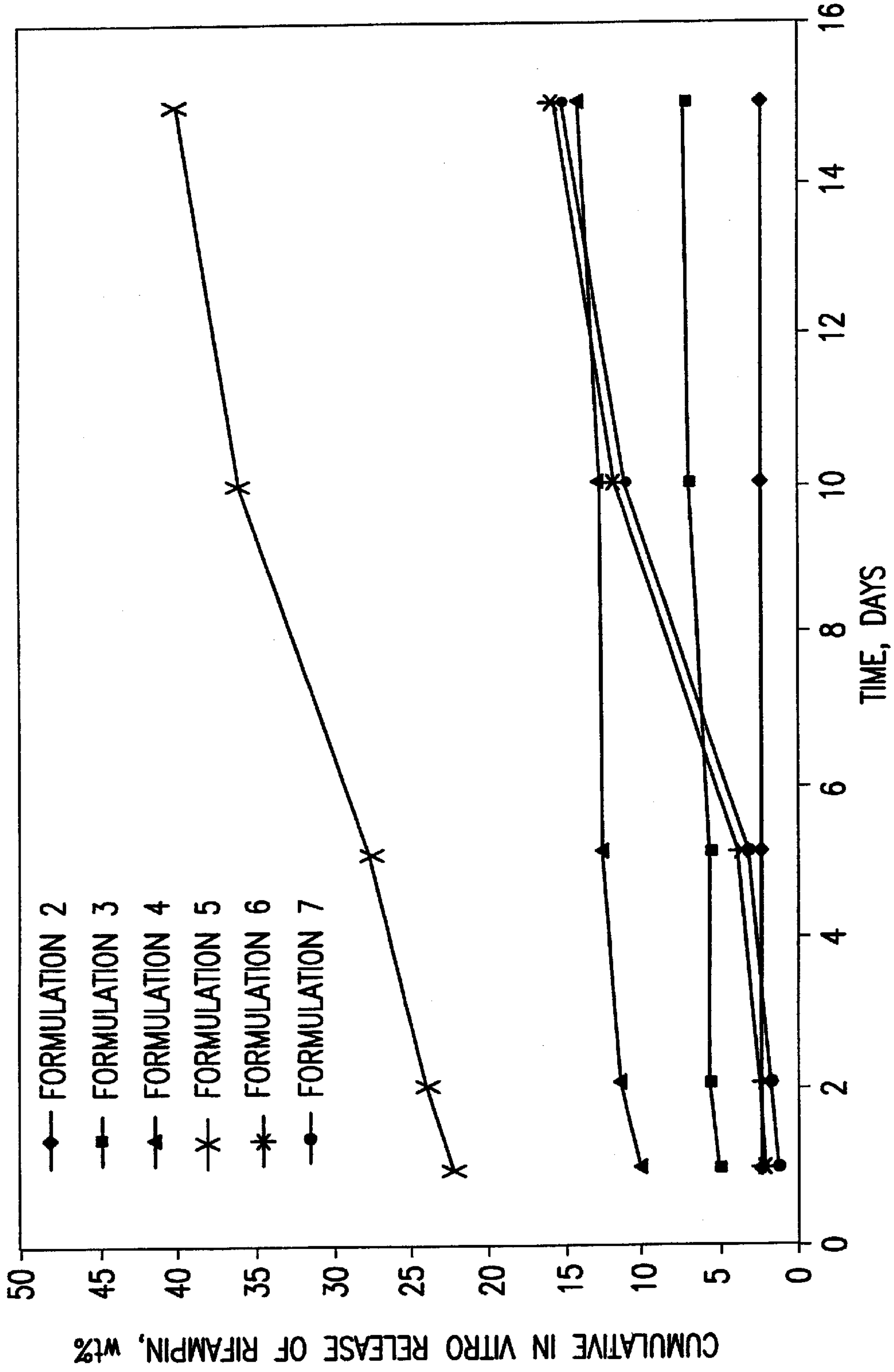
FIG. 6 shows the in vitro release characteristics of rifampicin-loaded microsphere Formulations 2–7 from Example 2 over a fifteen-day period in receiving fluid.

Microspheres were sterilized by gamma irradiation (25 kGy) prior to use in mice. Each lot of microspheres was analyzed for drug content by spectrophotometric and HPLC assays, for size, by standard procedures using a Malvern Particle Size Analyzer and release characteristics prior to use in mice. Matching placebo formulations were made for each drug loaded preparation. Representative formulations, including observed drug content (wt %), size, and in vitro release characteristics, are given in Table 4 and FIG. 6.

Mice

Female CD-1 female mice (14–16 g) were obtained from Charles River Laboratories and maintained on a diet of Teklad sterilizable laboratory feed (Harlan) and water in a Biosafety Level III facility throughout the studies.

Infection and Treatment of Mice

Mice were inoculated via the lateral tail vein on Day 0 with approximately $10^5$ viable bacilli of *Mycobacterium tuberculosis,* strain H37Rv in a volume of 0.1 ml 0.9% sterile sodium chloride solution. Drug treatments were initiated approximately 2 to 4 hours post-inoculation. Each treatment group contained ten mice. Formulations of the small microspheres, placebo and rifampicin-loaded, were injected intra peritoneally on Days 0 and 7 in a 32–50 mg dose suspended in a volume of 0.25 ml sterile saline using a sterile tuberculin syringe with a 23 gauge needle. Formulations of large microspheres from lots 6 and 7, placebo and rifampicin-loaded, were administered subcutaneously in a 100 mg dose suspended in a 0.5 ml volume of vehicle consisting of 0.5 wt % carboxymethylcellulose with 0.1 wt % Tween 80 and 5.0 wt % mannitol, on Day 0 only, over the dorsal thoracolumbar area using an 18-gauge needle attached to a sterile tuberculin syringe. Mice were maintained under general anesthesia with ketamine-xylazine (10 mg/100 gram body weight and 1.5 mg/100 gram body weight, respectively, given intramuscularly) during the subcutaneous injections. Oral gavage of rifampicin was performed daily from Day 0 to Day 25. A dosing rate of 0.1 ml per 10 gram body weight was administered daily to each mouse on individual weight with a solution of rifampicin yielding the following doses: 36, 20, 10, 5, 1.25 and 0.42 mg/kg. Mice were restrained and dosed by gavage using a stainless steel gavage needle attached to a tuberculin syringe. All mice were weighed daily and observed for clinical signs of toxicity. On Day 26, mice were euthanized with carbon dioxide inhalation for aseptic collection of lungs and spleens. Organs were frozen individually in sterile Tekmar bags, thawed, hand homogenized with a Bayer roller, diluted with sterile saline containing 0.05% Tween 80, and plated onto OADC-supplemented 7HII Middlebrook Mycobacterium solid agar. Colonies were enumerated after 14 to 21 days of incubation in a 37° C., 5% $CO_2$ incubator.

TABLE 4

Representative formulations of rifampicin-loaded microspheres.

| Formulation Number (Lot Number) | Excipient | Excipient Solvent | Rifampicin Content, wt % Theoretical | / Observed | Microsphere Size, μm[a] | In vitro Release (5) after 2 days |
|---|---|---|---|---|---|---|
| 1 (1290-00) | 60:40 DL-PLG | Ethyl Acetate | 30 | 1.38 | 101.1 | NA |
| 2 (1290-006) | 60:40 DL-PLG | Ethyl Acetate | 30 | 18 | 106.1 | 2 |
| 3 (1290-031) | 50:50 DL:PLG | Methylene Chloride | 30 | 19 | 110.7 | 5 |
| 4 (1290-049) | 65:35 DL-PLG | Ethyl Acetate | 30 | 17.6 | 68.4 | 15 |
| 5 (1290-107) | 60:40 DL-PLG[b] | Ethyl Acetate | 30 | 17 | 106.1 | 25 |
| 6 (1290-104) | 60:40/50:50 DL-PLG[c] | Ethyl Acetate | 30 | 27 | 101.1 | 2.5 |
| 7 (1463-038) | 60:40/50:50 DL-PLG[c] | Ethyl Acetate | 30 | 25.7 | 130.2 | 1.8 |

Figure 7A:
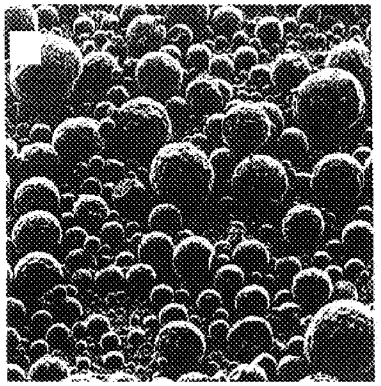
FIGS. 7A, 7B, and 7C are scanning electron micrographs of large rifampicin-loaded microsphere Formulation 7 from Example 2.
Figure 7B:
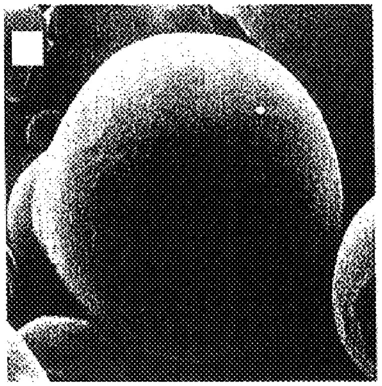
Figure 7C:
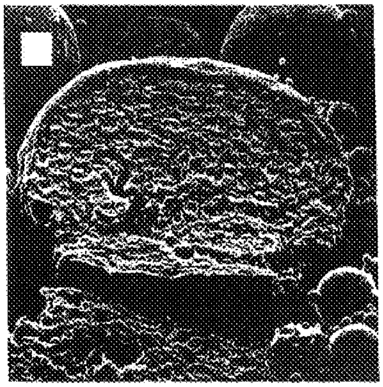
Figure 8A:
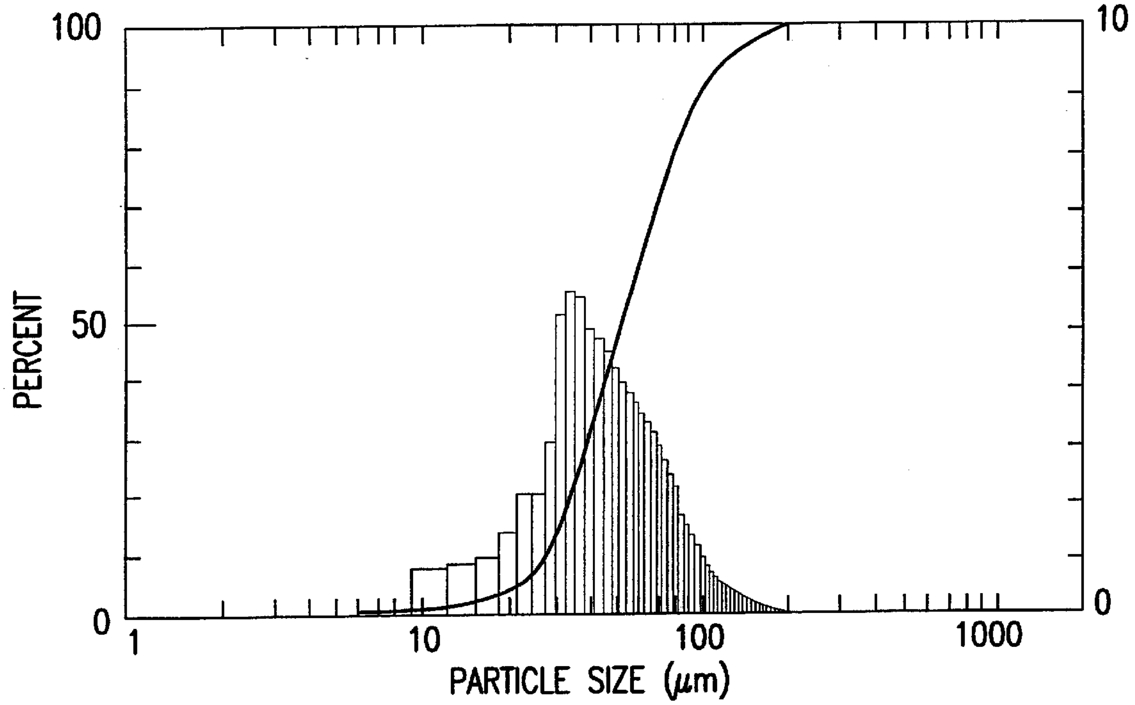
FIGS. 8A and 8B show the size distribution of rifampicin-loaded microsphere Formulations 6 and 7 from Example 2 as determined with a Malvern particle size analyzer.
Figure 8B:
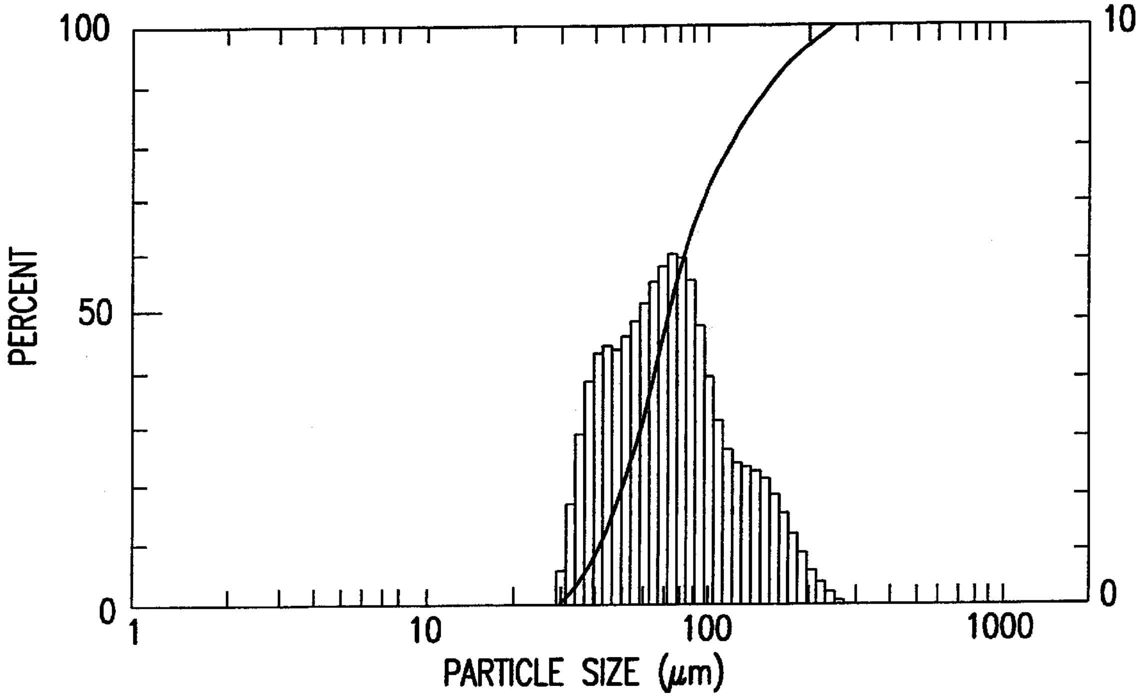

[a]Data reported as 90 volume percentiles.
[b]Microspheres prepared incorporating dextrose
[c]Excipient is a blend of 60:40 DL-PLG and low molecular weight 50:50 DL-PLG Microsphere formulations were also evaluated for surface morphology and size distribution in order to insure optimum delivery and release parameters. Typical morphology of the large microspheres is represented in FIGS. 7A, and 7B which depicts a cross section of a representative large microsphere. Size distributions, as determined by using a Malvern Particle Size Analyzer, are given for Formulations 6 and 7 in FIGS. 8A and 8B.

Free Rifampicin Preparation

Rifampicin (Sigma Chemical Company, St. Louis) was also prepared as a suspension for daily oral gavage in a solution of 10% dimethylsulfoxide (DMSO, tissue culture grade, Sigma) in sterile 0.9% sodium chloride (for injection, Baxter) solution.

Preparation of Small (1–10 micron) Rifampicin Microspheres

Small microspheres were prepared as in lots 5 and 6 in Example 1.

Mycobacterial Strains

*Mycobacterium tuberculosis* H37v (ATCC 27294, SRI #1345) was maintained as in Example 1.

Bioassay

A bioassay using *Staphylococcus aureus* (ATCC 29213), substantially as described in Example 1, was used to determine rifampicin concentrations in mouse plasma. The bioassay was modified slightly by preparing the standard curve for rifampicin in filter-sterilized control mouse plasma instead of culture medium.

For removal of plasma samples to be assayed by bioassay, the following procedure was used. Briefly, mice were anesthetized with ketamine-xylazine anesthesia for aseptic blood collection using a sterile tuberculin syringe with heparinized needle to withdraw volumes of 0.5 to 1.0 ml of blood from the heart. Mice were immediately euthanized with $C0_2$ following blood collection. Blood was centrifuged briefly and plasma was collected and frozen at −70° C. until assay.

Effects of Microsphere Preparations on Mice

Figure 9A:
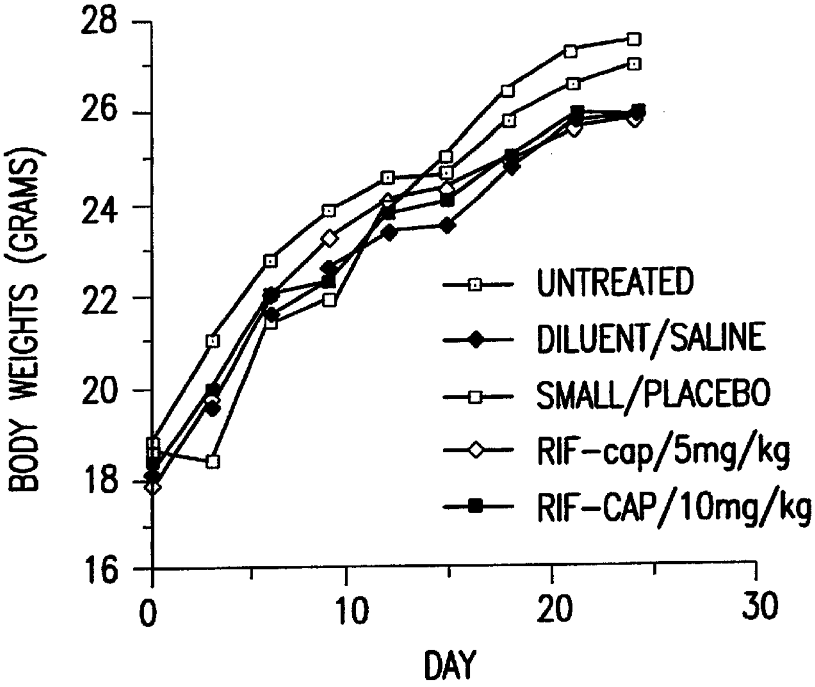
FIGS. 9A and 9B show a comparison of mice body weights following injection of small and large microspheres, respectively.
Figure 9B:
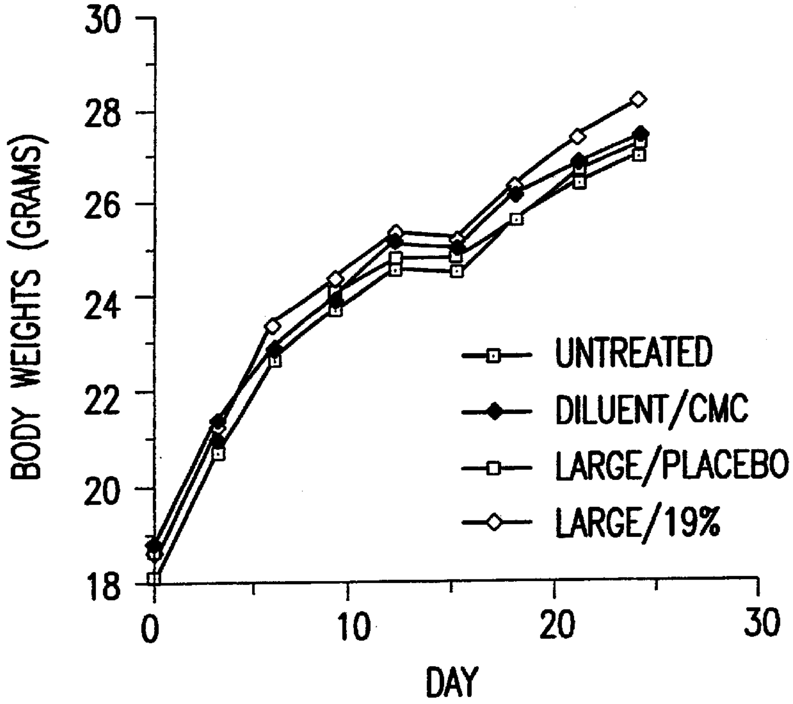

Generally, all microsphere preparations were well tolerated by the mice. For small microspheres, a slight reduction in mean body weights was recorded for groups of mice receiving small placebo on Day 3 (FIG. 9A). Some of those animals exhibited a slight ruffled coated appearance on Days 1 and 2. By Day 6, mice appeared clinically normal and had regained weight. Mice treated with placebo, or rifampicin-loaded large microspheres, tolerated the formulations very well (FIG. 9B). All mice exhibited normal clinical behavior, continued to consume feed and water, and did not exhibit abnormal behavior directed at the injection sites (i.e. chewing, biting). Following euthanasia, the postmortem examinations revealed subcutaneous deposits of microspheres in mice that had received the large preparations. Rifampicin-loaded preparations were still distinctly orange in color while placebo preparations were white. Similarly, intraperitoneal microspheres were observed in mice that had received the small preparations. Again, rifampicin-loaded microspheres were still distinctly orange in color while placebo preparations were white. Intraperitoneal administered microspheres adhered to various abdominal organs including spleen, liver, and intestines. The presence of microspheres did not appear to cause adhesions or other adverse conditions.

Release Characteristics in Mice

Figure 10:
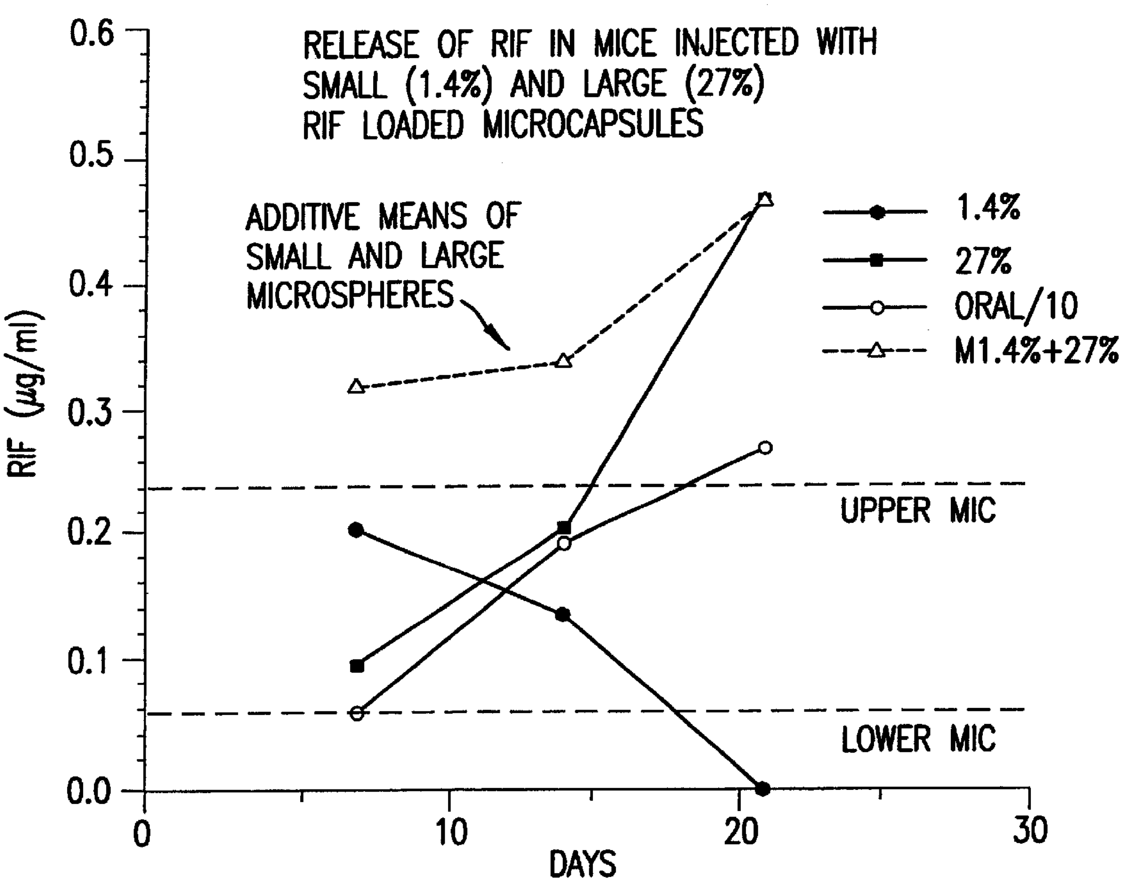
FIG. 10 shows the rifampicin release characteristics of mice injected with small and large rifampicin-loaded microspheres, versus mice that received daily administrations of free rifampicin.

Before experiments involving infected mice were conducted, release of rifampicin-loaded microspheres in vivo was quantified to rationalize the use of microspheres in an infected animal model. This was accomplished by injecting mice with either small or large microsphere formulations and orally administering free rifampicin, and subsequently monitoring plasma levels throughout an experimental period duplicating our infected animal model of 26 days. FIG. 10 depicts the results of that experiment.

Treatment of *M. tuberculosis* Infected Mice With Oral and Microsphere Formulations of Rifampicin Mice were infected with *M tuberculosis* H37Rv and either treated with oral doses of rifampicin or microsphere preparations of rifampicin. Oral doses of rifampicin were given daily for up to 25 days post-infection at quantities that varied from 0.42 mg rifampicin/kg to 10 mg rifampicin/kg/day. For mice receiving rifampicin in the form of large microspheres, only one treatment was administered at the time of infection. For mice receiving rifampicin by small microsphere formulations, two treatments were given. One was given at the time of infection and one was administered seven days post-infection. No other drag therapy was given to mice receiving microsphere formulations. Results are given in Tables 5 and 6.

Results of Example 2

With oral administration of rifampicin at concentrations of 0.42, 1.25, and 2.5 mg/kg, no significant reductions in viable *M. tuberculosis* H37Rv were observed at 26 days post-infection (Table 5). For mice receiving oral concentrations of 5.0 and 10 mg rifampicin/kg, significant reductions in viable *M tuberculosis* H37Rv were observed at 26 days post-infection (Table 5).

TABLE 5

Mice infected with *M. tuberculosis* H37Rv and treated with rifampicin orally. Data is reported in $\log_{10}$ CFU listings.

| Mouse Number | DMSO | 0.42 mg/kg | 1.25 mg/kg | 2.5 mg/kg | 5.0 mg/kg | 10 mg/kg |
|---|---|---|---|---|---|---|
| 1 | 5.69 | 5.86 | 5.97 | 5.56 | 5.45 | 4.27 |
| 2 | 5.6 | 5.66 | 5.71 | 5.30 | 5.31 | 4.72 |
| 3 | 5.83 | 5.59 | 5.69 | 5.87 | 5.10 | 4.15 |
| 4 | 5.52 | 5.72 | 5.64 | 5.2 | 5.43 | 4.00 |
| 5 | 5.61 | 5.95 | 5.47 | 5.11 | 5.06 | 3.48 |
| 6 | 5.7 | 5.88 | 5.44 | 5.69 | 5.18 | 4.54 |
| 7 | 5.51 | 5.86 | 5.62 | 5.44 | 5.20 | 3.30 |
| 8 | 5.75 | 5.7 | 5.88 | 5.79 | 5.18 | 3.00 |
| 9 | 6.02 | 6.15 | 5.72 | 5.67 | 5.51 | 4.48 |
| 10 | NA | NA | NA | 5.48 | 5.32 | NA |
| Mean | 5.69 | 5.62 | 5.68 | 5.51 | 5.27 | 3.99 |
| SEM | 0.05 | 0.06 | 0.06 | 0.08 | 0.05 | 0.20 |
| P | NA | >0.05 | >0.05 | >0.5 | <0.0001 | <0.0001 |

Treatment of *M. tuberculosis* H37Rv-infected mice with the small microsphere formulation alone did not result in a significant reduction in viable mycobacteria by 26 days (Table 6). However, treatment with either the large formulation or a combination of small and large formulations did result in a significant reduction in viable *M. tuberculosis* H37Rv by 26 days post-infection (Table 6). In addition, out of ten mice treated with the large formulation, two of those mice demonstrated no detectable CFUs by day 26 at the lowest dilution plated ($10^{-3}$) (Table 6). Likewise, out of ten mice treated with the small and large-microsphere combination, four of those demonstrated no detectable CFUs by day 26 at $10^{-3}$ dilution (Table 6). Three other groups, consisting of ten infected mice each, received placebo preparations of small, large and small plus large microspheres, respectively. No significant reduction in CFUs was observed in these groups after 26 days post-infection (data not reported).

TABLE 6

Mice infected with *M tuberculosis* H37Rv and treated with small (Formulation S6, 1.8 wt %), large (formulation 7, 25.7 wt %), and small + large microspheres (Formulations S6, and 7, respectively). Data reported in $log_{10}$ CFU in lungs.

| Mouse Number | DMSO $log_{10}$ CFU | Small Microspheres $log_{10}$ CFU | Large Microspheres $log_{10}$ CFU | Small + Large Microspheres $log_{10}$ CFU |
|---|---|---|---|---|
| 1 | 5.43 | 5.67 | 4.40 | 4.48 |
| 2 | 6.2 | 5.46 | 3.00 | 3.00[a] |
| 3 | 5.69 | 5.43 | 5.08 | 5.18 |
| 4 | 5.67 | 5.45 | 3.00[a] | 3.00[a] |
| 5 | 6.18 | 5.44 | 5.43 | 3.00[a] |
| 6 | 5.82 | 5.57 | 5.00 | 3.00[a] |
| 7 | 5.08 | 5.69 | 4.90 | 5.41 |
| 8 | 5.11 | 5.69 | 5.50 | 4.70 |
| 9 | 6.00 | 5.06 | 5.18 | 5.81 |
| 10 | 4.95 | NA | NA | 6.20 |
| Mean | 5.61 | 5.50 | 4.61 | 4.38 |
| SEM | 0.14 | 0.07 | 0.32 | 0.41 |
| P | NA | 0.50 | 0.008 | 0.03 |

[a]Lowest dilution was $10^{-3}$, therefore value of 3.0 represents no CFUs detected for these mice.

Post-therapy Plasma Levels of Rifampicin in Microsphere-treated Mice

Following the *M. tuberculosis* H37Rv infection experiment described above, plasma samples were processed from the mice immediately following termination of experiment. Plasma levels of rifampicin were then quantitated by the bioassay procedure. For mice that were treated with only the small rifampicin-microsphere formulation, four out of nine (44%) had detectable levels of rifampicin in their plasma, ranging from 0.11–0.20 μg/ml (Table 7). Five out of the nine receiving the small formulation had no detectable levels of rifampicin (Table 7). Plasma from mice treated with only the large rifampicin-microsphere formulation demonstrated detectable levels of rifampicin in six out of nine (67%), ranging from 0.15–2.69 μg/ml (Table 7). In the group of mice that received a combination of small and large rifampicin-loaded microspheres, nine out of nine mice (100%) had detectable levels of rifampicin in their plasma, ranging from 0.15–2.69 μg/ml (Table 7).

TABLE 7

Plasma levels in infected mice at 26 days post-infection (μg rifampicin/ml plasma). The small and large formulations were S6 (1.8 wt %) and 7 (25.7 wt %), respectively.

| Mouse Number | Small Microspheres | Large Microspheres | Small + Large Microspheres |
|---|---|---|---|
| 1 | 0.10 | 0.16 | 0.26 |
| 2 | 0.15 | 1.51 | 0.84 |
| 3 | 0.20 | 0.20 | 0.15 |
| 4 | 0.11 | 2.69 | 2.69 |
| 5 | <0.10 | 0.15 | 1.51 |
| 6 | <0.10 | 0.20 | 1.13 |
| 7 | <0.10 | <0.10 | 0.26 |
| 8 | <0.10 | <0.10 | 0.26 |
| 9 | <0.10 | <0.10 | 0.35 |
| Mean[a] | 0.14 | 0.82 | 0.83 |
| SEM | ±0.02 | ±0.43 | ±0.28 |
| Range | <0.10–0.20 | <0.10–2.69 | 0.15–2.69 |

[a]Mean reported for samples with detectable levels of rifampicin.

Example 3

In vivo Primate Studies

In the case of tuberculosis in primates, the MIC for rifampicin ranges from 0.06–0.25 μg rifampicin/ml. This concentration can be achieved in primates infected by *Mycobacterium tuberculosis* H37R, using the following injection schedule:

Day 0: Inject 2,000 mg of small microspheres (5.8 wt. % rifampicin), intravenously. Total rifampicin=116 mg Inject 2,000 mg of large microspheres (23 wt. % rifampicin), subcutaneously, at multiple sites. Total rifampicin=460 mg Day 7: Inject 2,000 mg of small microspheres (5.8 wt. % rifampicin), intravenously. Total rifampicin=116 mg Total rifampicin delivered by this method=692 mg Using this schedule, rifampicin is released for up to 30 days.

This dosage produces no toxic or adverse effects in noninfected primates.

Continued treatment in primates involves the following subsequent steps:

1. Repeat injection schedule after 30 days, assuming primate had no adverse reactions to the drug. Monitor liver function, etc. and take sputum cultures for tubercle bacilli.
2. Repeat injection every 30 days and monitor primate.
3. Continue this for at least 6 months.
4. Monitor primate for signs of tuberculosis.

Throughout this application, various publications are referenced. The disclosures of these publications in their entireties are hereby incorporated by reference into this application in order to more fully describe the state of the art to which this invention pertains.

This invention is not limited to specific synthetic methods, specific pharmaceutical carriers, or to particular pharmaceutical formulations or administration regimens, as such may, of course, vary. Similarly, the terminology used herein is for the purpose of describing particular embodiments only and is not intended to be limiting. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A method of treating or preventing a prokaryotic intracellular infection in an animal in need of such treatment or prevention comprising administering to the animal an effective amount of a suitable drug that can treat or prevent a prokaryotic intracellular infection in an animal, contained in biocompatible microspheres that have a diameter of from about 1 to about 10 microns, wherein the microspheres release the suitable drug upon administration at an effective rate, wherein the effective amount is an amount which is less than an effective amount of nonencapsulated drug, and wherein the biocompatible microsphere comprises a polymer, thereby treating or preventing the intracellular infection in the animal.

2. The method of claim 1 wherein the biocompatible microspheres have a diameter of from 1 to 5 microns.

3. The method of claim 1 wherein the biocompatible microspheres have a diameter of from 5 to 10 microns.

4. The method of claim 1 wherein the intracellular infection resides in the macrophage.

5. The method of claim 1 wherein the intracellular infection is tuberculosis.

6. The method of claim 1 wherein the intracellular infection is tuberculosis and the suitable drug is a rifamycin, a macrolide, a quinoline, or a combination thereof.

7. The method of claim 1 wherein the intracellular infection is tuberculosis and the suitable drug is rifampicin or rifabutin.

8. The method of claim 1 wherein the intracellular infection is associated with AIDS.

9. The method of claim 1 wherein the intracellular infection is caused by *M. avium.*

10. The method of claim 1 wherein the intracellular infection is caused by *M. avium,* and the suitable drug is a rifamycin, clofazimine, ciprofloxacin, parenteral amikacin, sparfloxacin, or a combination thereof.

11. The method of claim 1 wherein the intracellular infection is caused by *M. avium,* and the suitable drug is rifabutin.

12. The method of claim 1 wherein the administering of the microspheres is by intravenous administration.

13. The method of claim 1 wherein the microspheres comprise a poly(lactide) or poly (lactide-co-glycolide) matrix.

14. The method of claim 1 wherein the microspheres comprise a poly(anhydride) or poly(caprolactone) matrix.

15. The method of claim 1 further comprising administering the microspheres a second time.

16. The method of claim 1 wherein the administration is ex vivo.

17. The method of claim 1 wherein the animal is a human.

18. The method of claim 1 wherein the method is for treating an intracellular infection.

19. The method of claim 1 wherein the method is for preventing an intracellular infection.

20. The method of claim 1 further comprising administering nonencapsulated drug to the animal.

21. A method of treating or preventing tuberculosis in an animal in need of such treatment or prevention comprising administering to the animal an effective amount of a suitable drug that can treat or prevent tuberculosis in an animal, contained in biocompatible microspheres that have a diameter of from about 1 to about 10 microns, wherein the microspheres release the suitable drug upon administration at an effective rate, and wherein the effective amount is an amount which is less than an effective amount of nonencapsulated drug, thereby treating or preventing the tuberculosis in the animal.

22. The method of claim 21 wherein the biocompatible microspheres have a diameter of from 1 to 5 microns.

23. The method of claim 21 wherein the biocompatible microspheres have a diameter of from 5 to 10 microns.

24. The method of claim 21 wherein the suitable drug is a rifamycin, a macrolide, a quinoline, or a combination thereof.

25. The method of claim 21 wherein the suitable drug is rifampicin or rifabutin.

26. The method of claim 21 wherein the administering of the microspheres is by intravenous administration.

27. The method of claim 21 wherein the microspheres comprise a poly(lactide) or poly (lactide-co-glycolide) matrix.

28. The method of claim 21 further comprising administering the microspheres a second time.

29. The method of claim 21 wherein the animal is a human.

30. A method of treating or preventing a prokaryotic intracellular infection in an animal in need of such treatment or prevention comprising administering to the animal an effective amount of a suitable drug that can treat or prevent a prokaryotic intracellular infection in an animal, contained in biocompatible microspheres that have a diameter of less than or equal to 10 microns, wherein the microspheres release the suitable drug upon administration at an effective rate, wherein the effective amount is an amount which is less than an effective amount of nonencapsulated drug, and wherein the biocompatible microsphere comprises a polymer, thereby treating or preventing the intracellular infection in the animal.

31. The method of claim 1, wherein the polymer comprises a poly(diene), a poly(alkene), a poly(acrylic), a poly (methacrylic), a poly(vinyl ether), a poly(vinyl alcohol), a poly(vinyl ketone), a poly(vinyl halide), a poly(vinyl nitrile), a poly(vinyl ester), a poly(vinyl pyridine), a poly (styrene), a poly(cabonate), a poly(ester), a poly(orthoester), a poly(esteramide), a poly(anhydride), a poly(urethane), a poly(amide), a poly(lactide), poly(glycolide), poly (caprolactone), poly(hydroxybutyrate), poly(lactide-co-glycolide), a cellulose ether, cellulose ester, a poly (saccharide), a protein, a gelatin, a starch, a gum, a resin, or a combination thereof.

32. A method of treating or preventing a prokaryotic intracellular infection in an animal in need of such treatment or prevention comprising administering to the animal (1) a first effective amount of a first suitable drug contained in first biocompatible microspheres that have a diameter of from about 1 to about 10 microns, wherein the first microspheres release the first suitable drug upon administration, and (2) a second effective amount of a second suitable drug contained in second biocompatible microspheres that have a diameter of greater than about 10 microns, wherein the second microspheres release the second suitable drug upon administration, and wherein the first suitable drug is the same or different than the second suitable drug, thereby treating or preventing the intracellular infection in the animal.

33. The method of claim 32 wherein the first suitable drug is the same as the second suitable drug.

34. The method of claim 32 wherein the second microspheres are less than 500 microns in diameter.

35. The method of claim 32 wherein the second microspheres are less than 150 microns in diameter.

36. The method of claim 32 wherein the administering of the second microspheres is by subcutaneous administration.

37. The method of claim 32 wherein the second microspheres comprise a poly(lactide) or poly (lactide-co-glycolide).

38. The method of claim 32 wherein the second microspheres comprise a poly(anhydride) or poly(caprolactone).

39. The method of claim 32 further comprising administering the second microspheres a second tine.

40. The method of claim 32 further comprising administering nonencapsulated drug to the animal.

41. A method of treating or preventing tuberculosis in an animal in need of such treatment or prevention comprising administering to the animal (1) a first effective amount of a first suitable drug contained in first biocompatible microspheres that have a diameter of from about 1 to about 10 microns, wherein the first microspheres release the first suitable drug upon administration, and (2) a second effective amount of a second suitable drug contained in second biocompatible microspheres that have a diameter of greater than about 10 microns, wherein the second microspheres release the second suitable drug upon administration, and wherein the first suitable drug is the same or different than the second suitable drug, thereby treating or preventing the tuberculosis in the animal.

42. The method of claim 41 wherein the first suitable drug is the same as the second suitable drug.

43. The method of claim 41 wherein the second microspheres are less than 500 microns in diameter.

44. The method of claim 41 wherein the second microspheres are less than 150 microns in diameter.

45. The method of claim 41 wherein the administering of the second microspheres is by subcutaneous administration.

46. The method of claim 41 wherein the second microspheres comprise a poly(lactide) or poly (lactide-co-glycolide).

47. The method of claim 41 further comprising administering the second microspheres a second time.

48. The method of claim 41 further comprising administering nonencapsulated drug to the animal.

* * * * *